US007049137B2

(12) United States Patent
Jegla

(10) Patent No.: US 7,049,137 B2
(45) Date of Patent: May 23, 2006

(54) KCNQ5, A NOVEL POTASSIUM CHANNEL

(75) Inventor: Timothy J. Jegla, Durham, NC (US)

(73) Assignee: Icagen, Inc., Durham, NC (US)

( * ) Notice: Subject to any disclaimer, the term of this patent is extended or adjusted under 35 U.S.C. 154(b) by 0 days.

(21) Appl. No.: 09/810,796

(22) Filed: Mar. 15, 2001

(65) Prior Publication Data

US 2002/0102677 A1   Aug. 1, 2002

Related U.S. Application Data

(60) Provisional application No. 60/190,954, filed on Mar. 21, 2000.

(51) Int. Cl.
C07K 14/00 (2006.01)
C07H 21/04 (2006.01)
C12N 5/10 (2006.01)
C12N 15/09 (2006.01)

(52) U.S. Cl. ............... 435/325; 435/252.3; 435/320.1; 530/350; 536/23.1; 536/23.5

(58) Field of Classification Search ............... 530/300, 530/350; 536/23.1, 23.5; 435/325, 320.1, 435/252.3, 69.1, 70.1
See application file for complete search history.

(56) References Cited

U.S. PATENT DOCUMENTS 6,649,371 B1 * 11/2003 Jentsch ................. 435/69.1
6,767,736 B1 *  7/2004 Hu et al. .............. 435/320.1

FOREIGN PATENT DOCUMENTS

| WO | WO 99/07832 A1 | 2/1999 |
| WO | WO 00/61606 | 10/2000 |
| WO | WO 00/77035 A2 | 12/2000 |
| WO | WO-0170759 | * 9/2001 |
| WO | WO-0175108 | * 11/2001 |

OTHER PUBLICATIONS

Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Schroeder et al. KCNQ5, a novel potassium channel broadly expressed in brain, mediates M-tye currents. J Biol Chem 275(31): 24089-24095, 2000.*
Lehmann-Horn et al. Voltage-gated ion channels and hereditary disease. Pharmacol Rev 79(4): 1317-1372, 1999.*
Robbins et al. KCNQ potassium channels: physiology, pathophysiology, and pharmacology. Pharmacol Ther. 90(1)1-19, 2001.*
Wickenden, AD et al. Characterization of KCNQ5/Q3 potassium channels expressed in mammalian cells. Br J Pharmacol. 132(2):381-384, 2001.*
Jegla et al. Cloning and expression of human KCNQ5, a novel member of the KCNQ potassium channel family. Soc Neurosci Abs 26(1-2): 714.1, 2000.*
Kaufman et al. Blood 94: 3178-3184, 1999.*
Wang et al. Rapid analysis of gene expression (RAGE) facilitates universal expression profiling. Nucleic Acids Res 27(23): 4609-4618, 1999.*
Philips, A., The challenge of gene therapy and DNA delivery. J Pharm Pharmacology 53: 1169-1174, 2001.*
Lerche, et al. "Moleuclar Cloning and Functional Expression of KCNQ5, a Potassium Channel Subunit that May contribute to Neuronal M-current Diversity" J. of Biological Chemistry (2000) vol. 275(29), pp. 22395-22400.
Kubisch et al. -& Database EMBL 'Online! Retrieved from EBI Database, Accession No. AF105202, Mar. 3, 2000.
Kubisch et al. -& Database EMBL 'Online! Retrieved from EBI Database, Accession No. P56696, Jul. 15, 1999.
Biervert, et al., "A Potassium Channel Mutation in Neonatal Human Epilepsy"; Science, 279:403-406 (Jan. 1998).
Charlier, et al., "A Pore Mutation in a Novel KQT-like Potassium Channel Gene in an Idiopathic Epilepsy Family"; Nature Genetics, 18:53-55 (Jan. 1998).

(Continued)

Primary Examiner—Elizabeth Kemmerer
Assistant Examiner—Bridget E. Bunner
(74) Attorney, Agent, or Firm—Townsend and Townsend and Crew LLP

(57) ABSTRACT

The invention provides isolated nucleic acid and amino acid sequences of KCNQ5, antibodies to KCNQ5, methods of detecting KCNQ5, methods of screening for potassium channel activators and inhibitors using biologically active KCNQ5, and kits for screening for activators and inhibitors of voltage-gated potassium channels comprising KCNQ5.

5 Claims, 5 Drawing Sheets

OTHER PUBLICATIONS

Kubisch, et al., "KCNQ4, a Novel Potassium Channel Expressed in Sensory Outer Hair Cells, Is Mutated in Dominant Deafness"; *Cell*, 96:437-446 (Feb. 1999).

Singh, et al., "A Novel Potassium Channel Gene, KCNQ2, Is Mutated in an Inherited Epilepsy of Newborns"; *Nature Genetics*, 18:25-29 (Jan. 1998).

Wang, et al., "Positional Cloning of a Novel Potassium Channel Gene: KVLQT1 Mutations Cause Cardiac Arrhythmias"; *Nature Genetics*, 12:17-23 (Jan. 1996).

Wang, et al., "KCNQ2 and KCNQ3 Potassium Channel Subunits: Molecular Correlates of the M-Channel"; *Science*, 282:1890-1893 (Dec. 1998).

Yang, et al., "Functional Expression of Two $K_vLQT1$-related Potassium Channels Responsible for an Inherited Idiopathic Epilepsy"; *The Journal of Biological Chemistry*, 273:19419-19423 (Jul. 1998).

Kananura, et al., "The New Voltage Gated Potassium Channel KCNQ5 and Neonatal Convulsions"; *Genetics of Nervous System Diseases*, 11-2063-2067 (Jun. 2000).

* cited by examiner

| 1   | MKDVESGRGRVLLNSAAARGDGLLLLGTRAATLGGGGGLRESRRGKQGARMSLLGKPLSYTSSQSCRRNVKYRRVQNYL | kcnq5- |
| 1   | MKDVESGRGRVLLNSAAARGDGLLLLGTRAATLGGGGGLRESRRGKQGARMSLLGKPLSYTSSQSCRRNVKYRRVQNYL | kcnq5- |

| 81  | YNVLERPRGWAFIYHAFVFLLVFGCLILSVFSTIPEHTKLASSCLLILEFVMIVVFGLEFIIRIWSAGCCCRYRGWQGRL | kcnq5- |
| 81  | YNVLERPRGWAFIYHAFVFLLVFGCLILSVFSTIPEHTKLASSCLLILEFVMIVVFGLEFIIRIWSAGCCCRYRGWQGRL | kcnq5- |

| 161 | RFARKPFCVIDTIVLIASIAVVSAKTQGNIFATSALRSLRFLQILRMVRMDRRGGTWKLLGSVVYAHSKELITAWYIGFL | kcnq5- |
| 161 | RFARKPFCVIDTIVLIASIAVVSAKTQGNIFATSALRSLRFLQILRMVRMDRRGGTWKLLGSVVYAHSKELITAWYIGFL | kcnq5- |

| 241 | VLIFSSFLVYLVLVEKDANKEFSTYADALWWGTITLTTIGYGDKTPLTWLGRLLSAGFALLGISFFALPAGILGSGFALKVQ | kcnq5- |
| 241 | VLIFSSFLVYLVLVEKDANKEFSTYADALWWGTITLTTIGYGDKTPLTWLGRLLSAGFALLGISFFALPAGILGSGFALKVQ | kcnq5- |

| 321 | EQHRQKHFEKRRNPAANLIQCVWRSYAADEKSVSIATWKPHLKALHTCSPTKKEQCEASSSQKLSFKERVRMASPRGQSI | kcnq5- |
| 321 | EQHRQKHFEKRRNPAANLIQCVWRSYAADEKSVSIATWKPHLKALHTCSPTN------QKLSFKERVRMASPRGQSI | kcnq5- |

| 401 | KSRQASVGDRRSPSTDITAEGSPTKVQKSWSFNDRTRFRPSLRLKSSQPKPVIDADTALGTDDVYDEKGCQCDVSVEDLT | kcnq5- |
| 392 | KSRQASVGDRRSPSTDITAEGSPTKVQKSWSFNDRTRFRPSLRLKSSQPKPVIDADTALGTDDVYDEKGCQCDVSVEDLT | kcnq5- |

| 481 | PPLKTVIRAIRIMKFHVAKRKRKKETLRPYDVKDVIEQYSAGHLDMLCRIKSLQTRVDQILGKQITSDKKSREKITAEHE | kcnq5- |
| 472 | PPLKTVIRAIRIMKFHVAKRKRKKETLRPYDVKDVIEQYSAGHLDMLCRIKSLQTRVDQILGKQITSDKKSREKITAEHE | kcnq5- |

| 561 | TTDDLSMLGRVVKVEKQVQSIESKLDCLLDIYQQVLRKGSASALALASFQIPPFECEQTSDYQSPVDSKDLSGSAQNSGC | kcnq5- |
| 552 | TTDDLSMLGRVVKVEKQVQSIESKLDCLLDIYQQVLRKGSASALALASFQIPPFECEQTSDYQSPVDSKDLSGSAQNSGC | kcnq5- |

| 641 | LSRSTSANISRGLQFILTPNEFSAQTFYALSPTMHSQATQVPISQSDGSAVAATNTIANQINTAPKPAAPTTLQIPPPLP | kcnq5- |
| 632 | LSRSTSANISRGLQFILTPNEFSAQTFYALSPTMHSQATQVPISQSDGSAVAATNTIANQINTAPKPAAPTTLQIPPPLP | kcnq5- |

| 721 | AIKHLPRPETLHPNPAGLQESISDVTTCLVASKENVQAQSNLTKDRSMRKSFDMGGETLLSVCPMVPKDLGKSLSVQNL | kcnq5- |
| 712 | AIKHLPRPETLHPNPAGLQESISDVTTCLVASKENVQAQSNLTKDRSMRKSFDMGGETLLSVCPMVPKDLGKSLSVQNL | kcnq5- |

| 801 | IRSTEELNIQLSGSESSGSRGSQDFYPKWRESKLFITDEEVGPEETETDTFDAAPQPAREAAFASDSLRTGRSRSSQSIC | kcnq5- |
| 792 | IRSTEELNIQLSGSESSGSRGSQDFYPKWRESKLFITDEEVGPEETETDTFDAAPQPAREAAFASDSLRTGRSRSSQSIC | kcnq5- |

| 881 | KAGESTDALSLPHVKLK | kcnq5- |
| 872 | KAGESTDALSLPHVKLK | kcnq5- |

*FIG. 1.*

```
  1 MKDVESGRGRVLLNSAAARGDGLILGTRAATIGGGGGLRESBRGKQGARMSLLGKPIS----YTSSQSQRR------NVK          kcnq5.PR
  1 MVQ-KSRNGGVYPGPSGEKKLKVGFVGLDPGAPDSTRDGALLIAGSEAPKRGSILSKPRAGLGAGAGKPPKRNAF----           fiKCNQ2.PR
  1 MAEAPPRRLGLGPPGDAPRAEIVALTAVQSEQGEAGGGSPRRLLSPLPP-GAPIPGPGSSGSAGQRSSAAHKR                  fiKCNQ4.pr 73 YRRMQNYLYNVLERPRGWAFIYHAFVFLLVFGCLILSVFSTIPEHTKLASSCLLILEFVMIVVFGLEEIIRIWSAGCCCR          kcnq5.PR
 74 YNKLQNFLYNVLERPRGWAFIYHAYVFLLVFSCLVLSVFSTIKEYEKSSEGALYILEIIVVFGEYEYRIWAGCCCR              fiKCNQ2.PR
 80 YRRLQNWVYNVLERPRGWAFMYHVELLLVFSCLVLSVISTIQEHQELANECLLILEEVMIVVFGLEYIVRWSAGCCCR            fiKCNQ4.pr 153 YRGWQGRLRFARKPFCVIDIMVLIASIAVSAKTQGNIFATSALRSLRFLQILRMVRMDRRGGTWKLLGSVVYAHSKELI           kcnq5.PR
154 YRGWRGRIKFARKPFCVIDIMVLIASIAVLAAGSQGNVFATSALRSLRFLQILRMIRMDRRGGTWKLLGSVVYAHSKELV          fiKCNQ2.PR
160 YRGWQGRFRFARKPFCVIDFIVFVASVAVTAAGTQGNIFATSALRSMRFLQILRMVRMDRRGGTWKLLGSVVYAHSKELI          fiKCNQ4.pr 233 TAWYIGFLVLIFSSFLVYLVEKDANKEFSTYADALWGTILTLTTIGYGDKTPL.TWLGRLLISAGFALLGISFFALPAGILG         kcnq5.PR
234 TAWYIGFLIFLHSAFLVYLAEKGENDHFDTYADALWGTILTLTTIGYGDVTPQTWNGRLLAAIIGSFFALPAGILG              fiKCNQ2.PR
240 TAWYIGFLVLIFSAFLVYLAEKDANSDESSYADSLWGTILTLTTIGYGDKTPHTWLGRVLAAGFALLGISFFALPAGILG          fiKCNQ4.pr 313 SGFALKVQEEHRQKHFEKRRNPAANLIQCVWRSYAAD-EKSVSIATW--------------KPHLKA-                     kcnq5.PR
314 SGFALKVQEQHRQKHFEKRRNPAAGLIQSAWRFYATNLSRTDHSTWQYERTVTVPMYRLIPPI-NQLELIRNLKSKSG            fiKCNQ2.PR
320 SGFALKVQEQHRQKHFEKRRNPAANLIQAAWRLYATMYSTDMSRAYLIATWYYDSIL--PSFRLALIFEHVQRARNGGRP-        fiKCNQ4.pr 365 ---------------TCSPTKKEQEASSSQKISFKFRVRMASP--RGQSIKSRQAASVGDRRSPSTDLTAEG-SP              kcnq5.PR
393 LAFRKDPPEPSPS----------------QKVSLKDRV-FSSSPRGVAAKGKGSPQAQTVRRSPSADQSLED-SP              fiKCNQ2.PR
397 LEVRRAWDGAPSRYPPVATCHRPGSTSFCPGESRMGIKDRIRMGSSQRRTGPSKQQIAPRIMPTSPSSEQVGFATSP            fiKCNQ4.pr 424 TKVQKSWSFNDRTRFRIRSLRLKSSQPKPVIDADTALGTDVVDEKGCQCDVSVEDLTPPLKTVIRAIRIMKFHVAKRKFK         kcnq5.PR
450 SKVEKSWSFNDRTRFRAQARQAFRIKGAASRQNSE_EASLPGEDIVDDKSCPCEFVTEDLITPGLKVSIRACVMFLVSRKFK       fiKCNQ2.PR
477 TKVQKSWSFNDRTRFRASLRL--KPRTSAEDAFPSEFVAEKSYQCELTVDDIMPAVKTVIRSIRIIKFLVAKRKFK             fiKCNQ4.pr 504 ETLRPYDVKDVIEQYSAGHLDMLCRIKSLQTRVDQILGKQITSDKKSREKIT--AEHETTDLSMLGRVVKEKQVQS             kcnq5.PR
529 ELRPYDVMDVIEQYSAGHLDMISRIKSLQSRVDQIVGRPAITDKDR------TKGPAEAELPEDPSMGRLGKVEKQVLS          fiKCNQ2.PR
551 ETLRPYDVKDVIEQYSAGHLDMIGRIKSLQTRVDQIVGRGP--GDRAREKGDKGPSDAEVVDSISMMGRVVKEKQVQS           fiKCNQ4.pr
```

*FIG. 2*

```
581  IESKLDCLIDFYQQVLRKGSASAALALASFQFPEEQQLTSDYQSPVDSKDLSGSAQNSGQLSRSTSANISRGLQFILTPN  kcnq5.PR
605  MEKKLDFLVNIYMQLRMGIPPTETEAVEGAK--EPEPAPPYHSPEDSRE---HVDRHGQIVKIVRSSSSIG-----QK  fiKCNQ2.PR
629  IEHKLDLLLIGFMSRCLRSGTSASIG--AVQVELEDDITSDYHSPVDHEDISVSAQT------------------  fiKCNQ4.pr 661  EFSAQTFYALSFTMHSQATQVPISQSDGSAVAATNTIANQINTAPKPAAPTTLQPPPLPAIDHLPRPETLHPNPAGLQE  kcnq5.PR
672  NESAP---PAAEPVQCPPSTSWQPQSHPRQGHCLSPVGDH-----------GSLVRLPEPPAHERSLSAYGGNRASMEFL-  fiKCNQ2.PR
684  ------------------------------------------------------------------------  fiKCNQ4.pr 741  SISDVTTCLVASKENVQVAQSNITKDRSMRKSFDMGGETLSVCPMVPKDIGKSLSVQNLIRSTEFNIQDSGSESSGSR  kcnq5.PR
739  RQEDTPGQ-----------RPPEGTLI------RDSDLSLSIPSVDHEELERSFSGFSISQSKENLD-ALNSCYAAVAP  fiKCNQ2.PR
684  ----------------------------------LSISRSVSTNM-------------------------------  fiKCNQ4.pr 821  GSQDFYPKWRESKLFLTDEEVGPEETETDTFDAAPQFAREAAFASDSLRTGRSRSSQSICKAGESTDALSLPHVKLK.  kcnq5.PR
799  CAK------VRPYLAEGESDTDSDLCTPCGPPERSATGEGPFGDVGWAGPRK  fiKCNQ2.PR
695  ------D  fiKCNQ4.pr
```

FIG. 2

SEQUENCE LISTING

```
<160> NUMBER OF SEQ ID NOS: 17

<210> SEQ ID NO 1
<211> LENGTH: 3071
<212> TYPE: DNA
<213> ORGANISM: Homo sapiens
<220> FEATURE:
<223> OTHER INFORMATION: human outwardly rectifying, voltage-gated
      potassium channel KCNQ5-1
<221> NAME/KEY: CDS
<222> LOCATION: (10)..(2703)
<223> OTHER INFORMATION: KCNQ5-1

<400> SEQUENCE: 1
ggcagcggca tgaaggatgt ggagtcgggc cggggcaggg tgctgctgaa ctcggcagcc      60
gccaggggcg acggcctgct actgctgggc acccgcgcgg ccacgcttgg tggcggcggc     120
ggtggcctga gggagagccg ccggggcaag caggggcccc ggatgagcct gctggggaag     180
ccgctctctt acacgagtag ccagagctgc cggcgcaacg tcaagtaccg gcgggtgcag     240
aactacctgt acaacgtgct ggagagaccc cgcggctggg cgttcatcta ccacgctttc     300 gttttttctcc ttgtctttgg ttgcttgatt ttgtcagtgt tttctaccat ccctgagcac     360
acaaaattgg cctcaagttg cctcttgatc ctggagttcg tgatgattgt cgtctttggt     420
ttggagttca tcattcgaat ctggtctgcg ggttgctgtt gtcgatatag aggatggcaa     480
ggaagactga ggtttgctcg aaagcccttc tgtgttatag ataccattgt tcttatcgct     540
tcaatagcag ttgtttctgc aaaaactcag ggtaatattt tgccacgtc tgcactcaga      600 agtctccgtt tcctacagat cctccgcatg gtgcgcatgg accgaagggg aggcacttgg     660
aaattactgg gttcagtggt ttatgctcac agcaaggaat taatcacagc ttggtacata     720 ggattttttgg ttcttatttt ttcgtctttc cttgtctatc tggtggaaaa ggatgccaat     780
aaagagtttt ctacatatgc agatgctctc tggtggggca caattacatt gacaactatt     840
ggctatggag acaaaactcc cctaacttgg ctgggaagat tgctttctgc aggctttgca     900
ctccttggca tttcttttctt tgcacttcct gccggcattc ttggctcagg ttttgcatta     960
aaagtacaag aacaacaccg ccagaaacac tttgagaaaa gaaggaaccc agctgccaac    1020
ctcattcagt gtgtttggcg tagttacgca gctgatgaga atctgtttc cattgcaacc    1080 tggaagccac acttgaaggc cttgcacacc tgcagcccta ccaagaaaga acaaggggaa    1140
gcatcaagca gtcagaagct aagttttaag gagcgagtgc gcatggctag ccccagggc    1200 cagagtatta agagccgaca agcctcagta ggtgacagga ggtccccaag caccgacatc    1260
```

```
acagccgagg gcagtcccac caaagtgcag aagagctgga gcttcaacga ccgaacccgc   1320
ttccggccct cgctgcgcct caaaagttct cagccaaaac cagtgataga tgctgacaca   1380
gcccttggca ctgatgatgt atatgatgaa aaaggatgcc agtgtgatgt atcagtggaa   1440
gacctcaccc caccacttaa aactgtcatt cgagctatca gaattatgaa atttcatgtt   1500
gcaaaacgga agtttaagga aacrttacgt ccatatgatg taaaagatgt cattgaacaa   1560
tattctgctg gtcatctgga catgttgtgt agaattaaaa gccttcaaac acgtgttgat   1620
caaattcttg gaaaagggca atcacatca gataagaaga gccgagagaa ataacagca   1680 gaacatgaga ccacagacga tctcagtatg ctcggtcggg tggtcaaggt tgaaaaacag   1740
gtacagtcca tagaatccaa gctggactgc ctactagaca tctatcaaca ggtccttcgg   1800
aaaggctctg cctcagccct cgctttggct tcattccagt tcccacccttt tgaatgtgaa   1860 cagacatctg actatcaaag ccctgtggat agcaaagatc tttcgggttc cgcacaaaac   1920
agtggctgct tatccagatc aactagtgcc aacatctcga gaggcctgca gttcattctg   1980
acgccaaatg agttcagtgc ccagactttc tacgcgctta ccctactat gcacagtcaa   2040 gcaacacagg tgccaattag tcaaagcgat ggctcagcag tggcagccac caacaccatt   2100
gcaaaccaaa taaatacggc acccaagcca gcagccccaa caactttaca gatcccacct   2160
cctctcccag ccatcaagca tctgcccagg ccagaaactc tgcacctaa ccctgcaggc   2220 ttacaggaaa gcatttctga cgtcaccacc tgccttgttg cctccaagga aaatgttcag   2280
gttgcacagt caaatctcac caaggaccgt tctatgagga aaagctttga catgggagga   2340
gaaactctgt tgtctgtctg tcccatggtg ccgaaggact tgggcaaatc tttgtctgtg   2400
caaaacctga tcaggtcgac cgaggaactg aatatacaac tttcagggag tgagtcaagt   2460
ggctccagag gcagccaaga ttttacccc aaatggaggg aatccaaatt gtttataact   2520
gatgaagagg tgggtcccga agagacagag acagacactt ttgatgccgc accgcagcct   2580
gccagggaag ctgcctttgc atcagactct ctaaggactg gaaggtcacg atcatctcag   2640
agcatttgta aggcaggaga agtacagat gccctcagct tgcctcatgt caaactgaaa   2700
taagttcttc attttctttc caggcatagc agttctttag ccatacatat cattgcatga   2760
actatttcga aagcccttct aaaaagttga aattgcaaga atcgggaaga acatgaaagg   2820
cagtttataa gcccgttacc ttttaattgc atgaaaatgc atgtttaggg atggctaaaa   2880
ttccaaggtg catcgacatt aacccactca tttagtaatg taccttgagt taaaaagcct   2940
gagaaaccaa acacagctaa tgctatgggg tgtatgaata tgtcaagttt aggtcattta   3000
gaagatttga cactgtattt tgaaattatg ggagtaaaca ccttcaaatt tcaaaaaaaa   3060 aaaaaaaaa a                                                         3071
```

<210> SEQ ID NO 2
<211> LENGTH: 2694
<212> TYPE: DNA
<213> ORGANISM: Homo sapiens
<220> FEATURE:
<223> OTHER INFORMATION: human outwardly-rectifying, voltage-gated
      potassium channel KCNQ5-1 coding sequence
<221> NAME/KEY: CDS
<222> LOCATION: (1)..(2694)
<223> OTHER INFORMATION: KCNQ5-1

<400> SEQUENCE: 2

```
atgaaggatg tggagtcggg ccggggcagg gtgctgctga actcggcagc cgccagggc     60 gacggcctgc tactgctggg cacccgcgcg ccacgcttg gtggcggcgg cggtggcctg    120
```

-continued

```
agggagagcc gccggggcaa gcaggggggcc cggatgagcc tgctggggaa gccgctctct      180
tacacgagta gccagagctg ccggcgcaac gtcaagtacc ggcgggtgca gaactacctg      240
tacaacgtgc tggagagacc ccgcggctgg gcgttcatct accacgcttt cgttttcctc      300
cttgtctttg gttgcttgat tttgtcagtg ttttctacca tccctgagca cacaaaattg      360
gcctcaagtt gcctcttgat cctggagttc gtgatgattg tcgtctttgg tttggagttc      420
atcattcgaa tctggtctgc gggttgctgt tgtcgatata gaggatggca aggaagactg      480
aggtttgctc gaaagccctt ctgtgttata gataccattg ttcttatcgc ttcaatagca      540
gttgtttctg caaaaactca gggtaatatt tttgccacgt ctgcactcag aagtctccgt      600
ttcctacaga tcctccgcat ggtgcgcatg accgaaggg gaggcacttg gaaattactg      660
ggttcagtgg tttatgctca cagcaaggaa ttaatcacag cttggtacat aggattttg      720 gttcttattt tttcgtcttt ccttgtctat ctggtgggaaa aggatgccaa taaagagttt      780
tctacatatg cagatgctct ctggtggggc acaattacat tgacaactat tggctatgga      840
gacaaaactc ccctaacttg gctgggaaga ttgcttttctg caggctttgc actccttggc      900
atttcttcct ttgcacttcc tgccggcatt cttggctcag gttttgcatt aaaagtacaa      960
gaacaacacc gccagaaaca ctttgagaaa agaaggaacc cagctgccaa cctcattcag     1020
tgtgtttggc gtagttacgc agctgatgag aaatctgttt ccattgcaac ctggaagcca     1080
cacttgaagg ccttgcacac ctgcagccct accaagaaag aacaagggga agcatcaagc     1140
agtcagaagc taagttttaa ggagcgagtg cgcatggcta gccccagggg ccagagtatt     1200
aagagccgac aagcctcagt aggtgacagg aggtccccaa gcaccgacat cacagccgag     1260
ggcagtccca ccaaagtgca gaagagctgg agcttcaacg accgaacccg cttccggccc     1320
tcgctgcgcc tcaaaagttc tcagccaaaa ccagtgatag atgctgacac agcccttggc     1380
actgatgatg tatatgatga aaaaggatgc cagtgtgatg tatcagtgga agacctcacc     1440
ccaccactta aaactgtcat tcgagctatc agaattatga aatttcatgt tgcaaaacgg     1500
aagtttaagg aaacgttacg tccatatgat gtaaaagatg tcattgaaca atattctgct     1560
ggtcatctgg acatgttgtg tagaattaaa agccttcaaa cacgtgttga tcaaattctt     1620
ggaaaagggc aaatcacatc agataagaag agccgagaga aaataacagc agaacatgag     1680
accacagacg atctcagtat gctcggtcgg gtggtcaagg ttgaaaaaca ggtacagtcc     1740
atagagtcca agctggactg cctactagac atctatcaac aggtccttcg gaaaggctct     1800
gcctcagccc tcgctttggc ttcattccag atcccacctt ttgaatgtga acagacatct     1860
gactatcaaa gccctgtgga tagcaaagat ctttcgggtt ccgcacaaaa cagtggctgc     1920
ttatccagat caactagtgc caacatctcg agaggcctgc agttcattct gacgccaaat     1980
gagttcagtg cccagacttt ctacgcgctt agccctacta tgcacagtca agcaacacag     2040
gtgccaatta gtcaaagcga tggctcagca gtggcagcca ccaacaccat tgcaaaccaa     2100
ataaatacgg cacccaagcc agcagcccca acaactttac agatcccacc tcctctccca     2160
gccatcaagc atctgcccag gccagaaact ctgcacccta accctgcagg cttacaggaa     2220
agcatttctg acgtcaccac ctgccttgtt gcctccaagg aaaatgttca ggttgcacag     2280
tcaaatctca ccaaggaccg ttctatgagg aaaagctttg acatgggagg agaaactctg     2340
ttgtctgtct gtcccatggt gccgaaggac ttgggcaaat cttgtctgt gcaaaacctg     2400 atcaggtcga ccgaggaact gaatatacaa ctttcaggga gtgagtcaag tggctccaga     2460
```

```
ggcagccaag atttttaccc caaatggagg gaatccaaat tgtttataac tgatgaagag    2520
gtgggtcccg aagagacaga gacagacact tttgatgccg caccgcagcc tgccagggaa    2580
gctgcctttg catcagactc tctaaggact ggaaggtcac gatcatctca gagcatttgt    2640
aaggcaggag aaagtacaga tgccctcagc ttgcctcatg tcaaactgaa ataa          2694

<210> SEQ ID NO 3
<211> LENGTH: 2667
<212> TYPE: DNA
<213> ORGANISM: Homo sapiens
<220> FEATURE:
<223> OTHER INFORMATION: human outwardly rectifying, voltage-gated
      potassium channel KCNQ5-2 coding sequence
<221> NAME/KEY: CDS
<222> LOCATION: (1)..(2667)
<223> OTHER INFORMATION: KCNQ5-2

<400> SEQUENCE: 3
atgaaggatg tggagtcggg ccggggcagg gtgctgctga actcggcagc cgccagggc     60 gacggcctgc tactgctggg cacccgcgcg ccacgcttg gtggcggcgg cggtggcctg    120
agggagagcc gccggggcaa gcaggggcc cggatgagcc tgctggggaa gccgctctct    180
tacacgagta gccagagctg ccggcgcaac gtcaagtacc ggcgggtgca gaactacctg    240
tacaacgtgc tggagagacc ccgcggctgg gcgttcatct accacgcttt cgttttctc     300 cttgtctttg gttgcttgat tttgtcagtg ttttctacca tccctgagca cacaaaattg    360
gcctcaagtt gcctcttgat cctggagttc gtgatgattg tcgtctttgg tttggagttc    420
atcattcgaa tctggtctgc gggttgctgt tgtcgatata gaggatggca aggaagactg    480
aggtttgctc gaaagccctt ctgtgttata gataccattg ttcttatcgc ttcaatagca    540
gttgtttctg caaaaactca gggtaatatt tttgccacgt ctgcactcag aagtctccgt    600
ttcctacaga tcctccgcat ggtgcgcatg gaccgaaggg gaggcacttg aaaattactg    660
ggttcagtgg tttatgctca cagcaaggaa ttaatcacag cttggtacat aggatttttg    720
gttcttattt tttcgtcttt ccttgtctat ctggtgggaa aggatgccaa taaagagttt    780
tctacatatg cagatgctct ctggtggggc acaattacat tgacaactat ggctatgga    840 gacaaaactc ccctaacttg gctgggaaga ttgctttctg caggctttgc actccttggc    900
atttctttct ttgcacttcc tgccggcatt cttggctcag gttttgcatt aaaagtacaa    960
gaacaacacc gccagaaaca ctttgagaaa gaaggaacc cagctgccaa cctcattcag    1020
tgtgtttggc gtagttacgc agctgatgag aaatctgttt ccattgcaac ctggaagcca   1080
cacttgaagg cctgcacac ctgcagccct accaatcaga agctaagttt taaggagcga    1140
gtgcgcatgg ctagccccag gggccagagt attaagagcc gacaagcctc agtaggtgac    1200
aggaggtccc caagcaccga catcacagcc gagggcagtc ccaccaaagt gcagaagagc    1260
tggagcttca cgaccgaac ccgcttccgg ccctcgctgc gcctcaaaag ttctcagcca     1320
aaaccagtga tagatgctga cacagcccct tggcactgatg atgtatatga tgaaaaagga    1380
tgccagtgtg atgtatcagt ggaagacctc accccaccac ttaaaactgt cattcgagct    1440
atcagaatta tgaaatttca tgttgcaaaa cggaagttta aggaaacgtt acgtccatat    1500
gatgtaaaag atgtcattga acaatattct gctggtcatc tggacatgtt gtgtagaatt    1560
aaaagccttc aaacacgtgt tgatcaaatt cttggaaaag gcaaatcac atcagataag    1620 aagagccgag agaaaataac agcagaacat gagaccacag acgatctcag tatgctcggt    1680
cgggtggtca aggttgaaaa acaggtacag tccatagagt ccaagctgga ctgcctacta    1740
```

-continued

```
gacatctatc aacaggtcct tcggaaaggc tctgcctcag ccctcgcttt ggcttcattc    1800
cagatcccac cttttgaatg tgaacagaca tctgactatc aaagccctgt ggatagcaaa    1860
gatctttcgg gttccgcaca aaacagtggc tgcttatcca gatcaactag tgccaacatc    1920
tcgagaggcc tgcagttcat tctgacgcca aatgagttca gtgcccagac tttctacgcg    1980
cttagcccta ctatgcacag tcaagcaaca caggtgccaa ttagtcaaag cgatggctca    2040
gcagtggcag ccaccaacac cattgcaaac caaataaata cggcacccaa gccagcagcc    2100
ccaacaactt tacagatccc acctcctctc ccagccatca agcatctgcc caggccagaa    2160
actctgcacc ctaaccctgc aggcttacag gaaagcattt ctgacgtcac cacctgcctt    2220
gttgcctcca aggaaaatgt tcaggttgca cagtcaaatc tcaccaagga ccgttctatg    2280
aggaaaagct ttgacatggg aggagaaact ctgttgtctg tctgtcccat ggtgccgaag    2340
gacttgggca atctttgtc tgtgcaaaac ctgatcaggt cgaccgagga actgaatata    2400
caactttcag ggagtgagtc aagtggctcc agaggcagcc aagatttta ccccaaatgg    2460 agggaatcca aattgtttat aactgatgaa gaggtgggtc ccgaagagac agagacagac    2520
acttttgatg ccgcaccgca gcctgccagg gaagctgcct ttgcatcaga ctctctaagg    2580
actggaaggt cacgatcatc tcagagcatt tgtaaggcag gagaaagtac agatgccctc    2640
agcttgcctc atgtcaaact gaaataa                                        2667
```

<210> SEQ ID NO 4
<211> LENGTH: 897
<212> TYPE: PRT
<213> ORGANISM: Homo sapiens
<220> FEATURE:
<223> OTHER INFORMATION: human outwardly rectifying, voltage-gated
      potassium channel KCNQ5-1
<221> NAME/KEY: PEPTIDE
<222> LOCATION: (343)..(640)
<223> OTHER INFORMATION: conserved region of KCNQ5-1

<400> SEQUENCE: 4

Met Lys Asp Val Glu Ser Gly Arg Gly Arg Val Leu Leu Asn Ser Ala
 1               5                  10                  15

Ala Ala Arg Gly Asp Gly Leu Leu Leu Gly Thr Arg Ala Ala Thr
                20                  25                  30

Leu Gly Gly Gly Gly Gly Leu Arg Glu Ser Arg Arg Gly Lys Gln
            35                  40                  45

Gly Ala Arg Met Ser Leu Leu Gly Lys Pro Leu Ser Tyr Thr Ser Ser
     50                  55                  60

Gln Ser Cys Arg Arg Asn Val Lys Tyr Arg Arg Val Gln Asn Tyr Leu
 65                  70                  75                  80

Tyr Asn Val Leu Glu Arg Pro Arg Gly Trp Ala Phe Ile Tyr His Ala
                 85                  90                  95

Phe Val Phe Leu Leu Val Phe Gly Cys Leu Ile Leu Ser Val Phe Ser
                100                 105                 110

Thr Ile Pro Glu His Thr Lys Leu Ala Ser Ser Cys Leu Leu Ile Leu
            115                 120                 125

Glu Phe Val Met Ile Val Val Phe Gly Leu Glu Phe Ile Ile Arg Ile
        130                 135                 140

Trp Ser Ala Gly Cys Cys Cys Arg Tyr Arg Gly Trp Gln Gly Arg Leu
145                 150                 155                 160

Arg Phe Ala Arg Lys Pro Phe Cys Val Ile Asp Thr Ile Val Leu Ile
                165                 170                 175

```
Ala Ser Ile Ala Val Val Ser Ala Lys Thr Gln Gly Asn Ile Phe Ala
            180                 185                 190

Thr Ser Ala Leu Arg Ser Leu Arg Phe Leu Gln Ile Leu Arg Met Val
        195                 200                 205

Arg Met Asp Arg Arg Gly Gly Thr Trp Lys Leu Leu Gly Ser Val Val
    210                 215                 220

Tyr Ala His Ser Lys Glu Leu Ile Thr Ala Trp Tyr Ile Gly Phe Leu
225                 230                 235                 240

Val Leu Ile Phe Ser Ser Phe Leu Val Tyr Leu Val Glu Lys Asp Ala
                245                 250                 255

Asn Lys Glu Phe Ser Thr Tyr Ala Asp Ala Leu Trp Trp Gly Thr Ile
            260                 265                 270

Thr Leu Thr Thr Ile Gly Tyr Gly Asp Lys Thr Pro Leu Thr Trp Leu
        275                 280                 285

Gly Arg Leu Leu Ser Ala Gly Phe Ala Leu Leu Gly Ile Ser Phe Phe
    290                 295                 300

Ala Leu Pro Ala Gly Ile Leu Gly Ser Gly Phe Ala Leu Lys Val Gln
305                 310                 315                 320

Glu Gln His Arg Gln Lys His Phe Glu Lys Arg Arg Asn Pro Ala Ala
                325                 330                 335

Asn Leu Ile Gln Cys Val Trp Arg Ser Tyr Ala Ala Asp Glu Lys Ser
            340                 345                 350

Val Ser Ile Ala Thr Trp Lys Pro His Leu Lys Ala Leu His Thr Cys
        355                 360                 365

Ser Pro Thr Lys Lys Glu Gln Gly Glu Ala Ser Ser Ser Gln Lys Leu
    370                 375                 380

Ser Phe Lys Glu Arg Val Arg Met Ala Ser Pro Arg Gly Gln Ser Ile
385                 390                 395                 400

Lys Ser Arg Gln Ala Ser Val Gly Asp Arg Arg Ser Pro Ser Thr Asp
                405                 410                 415

Ile Thr Ala Glu Gly Ser Pro Thr Lys Val Gln Lys Ser Trp Ser Phe
            420                 425                 430

Asn Asp Arg Thr Arg Phe Arg Pro Ser Leu Arg Leu Lys Ser Ser Gln
        435                 440                 445

Pro Lys Pro Val Ile Asp Ala Asp Thr Ala Leu Gly Thr Asp Asp Val
    450                 455                 460

Tyr Asp Glu Lys Gly Cys Gln Cys Asp Val Ser Val Glu Asp Leu Thr
465                 470                 475                 480

Pro Pro Leu Lys Thr Val Ile Arg Ala Ile Arg Ile Met Lys Phe His
                485                 490                 495

Val Ala Lys Arg Lys Phe Lys Glu Thr Leu Arg Pro Tyr Asp Val Lys
            500                 505                 510

Asp Val Ile Glu Gln Tyr Ser Ala Gly His Leu Asp Met Leu Cys Arg
        515                 520                 525

Ile Lys Ser Leu Gln Thr Arg Val Asp Gln Ile Leu Gly Lys Gly Gln
    530                 535                 540

Ile Thr Ser Asp Lys Lys Ser Arg Glu Lys Ile Thr Ala Glu His Glu
545                 550                 555                 560

Thr Thr Asp Asp Leu Ser Met Leu Gly Arg Val Val Lys Val Glu Lys
                565                 570                 575

Gln Val Gln Ser Ile Glu Ser Lys Leu Asp Cys Leu Leu Asp Ile Tyr
            580                 585                 590
```

```
          Gln Gln Val Leu Arg Lys Gly Ser Ala Ser Ala Leu Ala Leu Ala Ser
                      595                 600                 605

Phe Gln Ile Pro Pro Phe Glu Cys Glu Gln Thr Ser Asp Tyr Gln Ser
                      610                 615                 620

Pro Val Asp Ser Lys Asp Leu Ser Gly Ser Ala Gln Asn Ser Gly Cys
          625                 630                 635                 640

Leu Ser Arg Ser Thr Ser Ala Asn Ile Ser Arg Gly Leu Gln Phe Ile
                          645                 650                 655

Leu Thr Pro Asn Glu Phe Ser Ala Gln Thr Phe Tyr Ala Leu Ser Pro
                      660                 665                 670

Thr Met His Ser Gln Ala Thr Gln Val Pro Ile Ser Gln Ser Asp Gly
                      675                 680                 685

Ser Ala Val Ala Ala Thr Asn Thr Ile Ala Asn Gln Ile Asn Thr Ala
          690                 695                 700

Pro Lys Pro Ala Ala Pro Thr Thr Leu Gln Ile Pro Pro Pro Leu Pro
          705                 710                 715                 720

Ala Ile Lys His Leu Pro Arg Pro Glu Thr Leu His Pro Asn Pro Ala
                          725                 730                 735

Gly Leu Gln Glu Ser Ile Ser Asp Val Thr Thr Cys Leu Val Ala Ser
                      740                 745                 750

Lys Glu Asn Val Gln Val Ala Gln Ser Asn Leu Thr Lys Asp Arg Ser
                      755                 760                 765

Met Arg Lys Ser Phe Asp Met Gly Gly Glu Thr Leu Leu Ser Val Cys
          770                 775                 780

Pro Met Val Pro Lys Asp Leu Gly Lys Ser Leu Ser Val Gln Asn Leu
          785                 790                 795                 800

Ile Arg Ser Thr Glu Glu Leu Asn Ile Gln Leu Ser Gly Ser Glu Ser
                          805                 810                 815

Ser Gly Ser Arg Gly Ser Gln Asp Phe Tyr Pro Lys Trp Arg Glu Ser
                      820                 825                 830

Lys Leu Phe Ile Thr Asp Glu Val Gly Pro Glu Glu Thr Glu Thr
                      835                 840                 845

Asp Thr Phe Asp Ala Ala Pro Gln Pro Ala Arg Glu Ala Ala Phe Ala
                      850                 855                 860

Ser Asp Ser Leu Arg Thr Gly Arg Ser Arg Ser Gln Ser Ile Cys
          865                 870                 875                 880

Lys Ala Gly Glu Ser Thr Asp Ala Leu Ser Leu Pro His Val Lys Leu
                          885                 890                 895

Lys

<210> SEQ ID NO 5
<211> LENGTH: 888
<212> TYPE: PRT
<213> ORGANISM: Homo sapiens
<220> FEATURE:
<223> OTHER INFORMATION: human outwardly rectifying, voltage-gated
      potassium channel KCNQ5-2

<400> SEQUENCE: 5

Met Lys Asp Val Glu Ser Gly Arg Gly Arg Val Leu Leu Asn Ser Ala
          1               5                   10                  15

Ala Ala Arg Gly Asp Gly Leu Leu Leu Gly Thr Arg Ala Ala Thr
                          20                  25                  30

Leu Gly Gly Gly Gly Gly Leu Arg Glu Ser Arg Arg Gly Lys Gln
                      35                  40                  45
```

```
Gly Ala Arg Met Ser Leu Leu Gly Lys Pro Leu Ser Tyr Thr Ser Ser
 50                  55                  60

Gln Ser Cys Arg Arg Asn Val Lys Tyr Arg Arg Val Gln Asn Tyr Leu
 65                  70                  75                  80

Tyr Asn Val Leu Glu Arg Pro Arg Gly Trp Ala Phe Ile Tyr His Ala
                 85                  90                  95

Phe Val Phe Leu Leu Val Phe Gly Cys Leu Ile Leu Ser Val Phe Ser
            100                 105                 110

Thr Ile Pro Glu His Thr Lys Leu Ala Ser Ser Cys Leu Leu Ile Leu
        115                 120                 125

Glu Phe Val Met Ile Val Val Phe Gly Leu Glu Phe Ile Ile Arg Ile
    130                 135                 140

Trp Ser Ala Gly Cys Cys Cys Arg Tyr Arg Gly Trp Gln Gly Arg Leu
145                 150                 155                 160

Arg Phe Ala Arg Lys Pro Phe Cys Val Ile Asp Thr Ile Val Leu Ile
                165                 170                 175

Ala Ser Ile Ala Val Val Ser Ala Lys Thr Gln Gly Asn Ile Phe Ala
            180                 185                 190

Thr Ser Ala Leu Arg Ser Leu Arg Phe Leu Gln Ile Leu Arg Met Val
        195                 200                 205

Arg Met Asp Arg Arg Gly Gly Thr Trp Lys Leu Leu Gly Ser Val Val
    210                 215                 220

Tyr Ala His Ser Lys Glu Leu Ile Thr Ala Trp Tyr Ile Gly Phe Leu
225                 230                 235                 240

Val Leu Ile Phe Ser Ser Phe Leu Val Tyr Leu Val Glu Lys Asp Ala
                245                 250                 255

Asn Lys Glu Phe Ser Thr Tyr Ala Asp Ala Leu Trp Trp Gly Thr Ile
            260                 265                 270

Thr Leu Thr Thr Ile Gly Tyr Gly Asp Lys Thr Pro Leu Thr Trp Leu
        275                 280                 285

Gly Arg Leu Leu Ser Ala Gly Phe Ala Leu Leu Gly Ile Ser Phe Phe
    290                 295                 300

Ala Leu Pro Ala Gly Ile Leu Gly Ser Gly Phe Ala Leu Lys Val Gln
305                 310                 315                 320

Glu Gln His Arg Gln Lys His Phe Glu Lys Arg Arg Asn Pro Ala Ala
                325                 330                 335

Asn Leu Ile Gln Cys Val Trp Arg Ser Tyr Ala Ala Asp Glu Lys Ser
            340                 345                 350

Val Ser Ile Ala Thr Trp Lys Pro His Leu Lys Ala Leu His Thr Cys
        355                 360                 365

Ser Pro Thr Asn Gln Lys Leu Ser Phe Lys Glu Arg Val Arg Met Ala
    370                 375                 380

Ser Pro Arg Gly Gln Ser Ile Lys Ser Arg Gln Ala Ser Val Gly Asp
385                 390                 395                 400

Arg Arg Ser Pro Ser Thr Asp Ile Thr Ala Glu Gly Ser Pro Thr Lys
                405                 410                 415

Val Gln Lys Ser Trp Ser Phe Asn Asp Arg Thr Arg Phe Arg Pro Ser
            420                 425                 430

Leu Arg Leu Lys Ser Ser Gln Pro Lys Pro Val Ile Asp Ala Asp Thr
        435                 440                 445

Ala Leu Gly Thr Asp Asp Val Tyr Asp Glu Lys Gly Cys Gln Cys Asp
    450                 455                 460

Val Ser Val Glu Asp Leu Thr Pro Pro Leu Lys Thr Val Ile Arg Ala
```

-continued

```
            465                 470                 475                 480
        Ile Arg Ile Met Lys Phe His Val Ala Lys Arg Lys Phe Lys Glu Thr
                        485                 490                 495
        Leu Arg Pro Tyr Asp Val Lys Asp Val Ile Glu Gln Tyr Ser Ala Gly
                        500                 505                 510
        His Leu Asp Met Leu Cys Arg Ile Lys Ser Leu Gln Thr Arg Val Asp
                        515                 520                 525
        Gln Ile Leu Gly Lys Gly Gln Ile Thr Ser Asp Lys Lys Ser Arg Glu
                        530                 535                 540
        Lys Ile Thr Ala Glu His Glu Thr Thr Asp Asp Leu Ser Met Leu Gly
        545                 550                 555                 560
        Arg Val Val Lys Val Glu Lys Gln Val Gln Ser Ile Glu Ser Lys Leu
                        565                 570                 575
        Asp Cys Leu Leu Asp Ile Tyr Gln Gln Val Leu Arg Lys Gly Ser Ala
                        580                 585                 590
        Ser Ala Leu Ala Leu Ala Ser Phe Gln Ile Pro Pro Phe Glu Cys Glu
                        595                 600                 605
        Gln Thr Ser Asp Tyr Gln Ser Pro Val Asp Ser Lys Asp Leu Ser Gly
                        610                 615                 620
        Ser Ala Gln Asn Ser Gly Cys Leu Ser Arg Ser Thr Ser Ala Asn Ile
        625                 630                 635                 640
        Ser Arg Gly Leu Gln Phe Ile Leu Thr Pro Asn Glu Phe Ser Ala Gln
                        645                 650                 655
        Thr Phe Tyr Ala Leu Ser Pro Thr Met His Ser Gln Ala Thr Gln Val
                        660                 665                 670
        Pro Ile Ser Gln Ser Asp Gly Ser Ala Val Ala Ala Thr Asn Thr Ile
                        675                 680                 685
        Ala Asn Gln Ile Asn Thr Ala Pro Lys Pro Ala Ala Pro Thr Thr Leu
                        690                 695                 700
        Gln Ile Pro Pro Pro Leu Pro Ala Ile Lys His Leu Pro Arg Pro Glu
        705                 710                 715                 720
        Thr Leu His Pro Asn Pro Ala Gly Leu Gln Glu Ser Ile Ser Asp Val
                        725                 730                 735
        Thr Thr Cys Leu Val Ala Ser Lys Glu Asn Val Gln Val Ala Gln Ser
                        740                 745                 750
        Asn Leu Thr Lys Asp Arg Ser Met Arg Lys Ser Phe Asp Met Gly Gly
                        755                 760                 765
        Glu Thr Leu Leu Ser Val Cys Pro Met Val Pro Lys Asp Leu Gly Lys
                        770                 775                 780
        Ser Leu Ser Val Gln Asn Leu Ile Arg Ser Thr Glu Glu Leu Asn Ile
        785                 790                 795                 800
        Gln Leu Ser Gly Ser Glu Ser Gly Ser Arg Gly Ser Gln Asp Phe
                        805                 810                 815
        Tyr Pro Lys Trp Arg Glu Ser Lys Leu Phe Ile Thr Asp Glu Val
                        820                 825                 830
        Gly Pro Glu Glu Thr Glu Thr Asp Thr Phe Asp Ala Ala Pro Gln Pro
                        835                 840                 845
        Ala Arg Glu Ala Ala Phe Ala Ser Asp Ser Leu Arg Thr Gly Arg Ser
                        850                 855                 860
        Arg Ser Ser Gln Ser Ile Cys Lys Ala Gly Glu Ser Thr Asp Ala Leu
        865                 870                 875                 880
        Ser Leu Pro His Val Lys Leu Lys
                        885
```

-continued

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:sense primer
      (1)

<400> SEQUENCE: 6
ccacgtctgc actcaggaag tctccg                                         26

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:antisense
      primer (2)

<400> SEQUENCE: 7
ccagcttgga ttctatggac tgtacc                                         26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:standard 3'
      RACE PCR gene specific primer (3)

<400> SEQUENCE: 8
gaagagccga gagaaaataa cagcag                                         26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:reamplification
      gene-specific oligo (4)

<400> SEQUENCE: 9
gccctgtgga tagcaaagat ctttcg                                         26

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:nested standard
      5' RACE PCR gene specific oligo (5)

<400> SEQUENCE: 10
gctgtgagca taaaccactg aaccc                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:nested standard
      5' RACE PCR gene specific oligo (6)

<400> SEQUENCE: 11
ccatgcgcac catgcggagg atctg                                          25

```
<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:amplification
      primer

<400> SEQUENCE: 12
catgaaggat gtggagtcgg g                                              21

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence:amplification
      primer

<400> SEQUENCE: 13
tggctaaaga actgctatgc ctgg                                           24

<210> SEQ ID NO 14
<211> LENGTH: 844
<212> TYPE: PRT
<213> ORGANISM: Homo sapiens
<220> FEATURE:
<223> OTHER INFORMATION: human KCNQ2

<400> SEQUENCE: 14
```

Met Val Gln Lys Ser Arg Asn Gly Gly Val Tyr Pro Gly Pro Ser Gly
 1               5                  10                  15

Glu Lys Lys Leu Lys Val Gly Phe Val Gly Leu Asp Pro Gly Ala Pro
             20                  25                  30

Asp Ser Thr Arg Asp Gly Ala Leu Leu Ile Ala Gly Ser Glu Ala Pro
         35                  40                  45

Lys Arg Gly Ser Ile Leu Ser Lys Pro Arg Ala Gly Gly Ala Gly Ala
     50                  55                  60

Gly Lys Pro Pro Lys Arg Asn Ala Phe Tyr Arg Lys Leu Gln Asn Phe
 65                  70                  75                  80

Leu Tyr Asn Val Leu Glu Arg Pro Arg Gly Trp Ala Phe Ile Tyr His
                 85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe

```
              225                 230                 235                 240
Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
                260                 265                 270

Ile Thr Leu Thr Thr Ile Gly Tyr Gly Asp Lys Tyr Pro Gln Thr Trp
            275                 280                 285

Asn Gly Arg Leu Leu Ala Ala Thr Phe Thr Leu Ile Gly Val Ser Phe
        290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
                340                 345                 350

Arg Thr Asp Leu His Ser Thr Trp Gln Tyr Tyr Glu Arg Thr Val Thr
            355                 360                 365

Val Pro Met Tyr Arg Leu Ile Pro Pro Leu Asn Gln Leu Glu Leu Leu
        370                 375                 380

Arg Asn Leu Lys Ser Lys Ser Gly Leu Ala Phe Arg Lys Asp Pro Pro
385                 390                 395                 400

Pro Glu Pro Ser Pro Ser Gln Lys Val Ser Leu Lys Asp Arg Val Phe
                405                 410                 415

Ser Ser Pro Arg Gly Val Ala Ala Lys Gly Lys Gly Ser Pro Gln Ala
                420                 425                 430

Gln Thr Val Arg Arg Ser Pro Ser Ala Asp Gln Ser Leu Glu Asp Ser
            435                 440                 445

Pro Ser Lys Val Pro Lys Ser Trp Ser Phe Gly Asp Arg Ser Arg Ala
        450                 455                 460

Arg Gln Ala Phe Arg Ile Lys Gly Ala Ala Ser Arg Gln Asn Ser Glu
465                 470                 475                 480

Glu Ala Ser Leu Pro Gly Glu Asp Ile Val Asp Asp Lys Ser Cys Pro
                485                 490                 495

Cys Glu Phe Val Thr Glu Asp Leu Thr Pro Gly Leu Lys Val Ser Ile
                500                 505                 510

Arg Ala Val Cys Val Met Arg Phe Leu Val Ser Lys Arg Lys Phe Lys
            515                 520                 525

Glu Ser Leu Arg Pro Tyr Asp Val Met Asp Val Ile Glu Gln Tyr Ser
        530                 535                 540

Ala Gly His Leu Asp Met Leu Ser Arg Ile Lys Ser Leu Gln Ser Arg
545                 550                 555                 560

Val Asp Gln Ile Val Gly Arg Gly Pro Ala Ile Thr Asp Lys Asp Arg
                565                 570                 575

Thr Lys Gly Pro Ala Glu Ala Glu Leu Pro Glu Asp Pro Ser Met Met
                580                 585                 590

Gly Arg Leu Gly Lys Val Glu Lys Gln Val Leu Ser Met Glu Lys Lys
            595                 600                 605

Leu Asp Phe Leu Val Asn Ile Tyr Met Gln Arg Met Gly Ile Pro Pro
        610                 615                 620

Thr Glu Thr Glu Ala Tyr Phe Gly Ala Lys Glu Pro Glu Pro Ala Pro
625                 630                 635                 640

Pro Tyr His Ser Pro Glu Asp Ser Arg Glu His Val Asp Arg His Gly
                645                 650                 655
```

```
Cys Ile Val Lys Ile Val Arg Ser Ser Ser Thr Gly Gln Lys Asn
            660                 665                 670

Phe Ser Ala Pro Pro Ala Ala Pro Pro Val Gln Cys Pro Pro Ser Thr
            675                 680                 685

Ser Trp Gln Pro Gln Ser His Pro Arg Gln Gly His Gly Thr Ser Pro
            690                 695                 700

Val Gly Asp His Gly Ser Leu Val Arg Ile Pro Pro Pro Pro Ala His
705                 710                 715                 720

Glu Arg Ser Leu Ser Ala Tyr Gly Gly Gly Asn Arg Ala Ser Met Glu
                725                 730                 735

Phe Leu Arg Gln Glu Asp Thr Pro Gly Cys Arg Pro Pro Glu Gly Thr
            740                 745                 750

Leu Arg Asp Ser Asp Thr Ser Ile Ser Ile Pro Ser Val Asp His Glu
            755                 760                 765

Glu Leu Glu Arg Ser Phe Ser Gly Phe Ser Ile Ser Gln Ser Lys Glu
            770                 775                 780

Asn Leu Asp Ala Leu Asn Ser Cys Tyr Ala Ala Val Ala Pro Cys Ala
785                 790                 795                 800

Lys Val Arg Pro Tyr Ile Ala Glu Gly Glu Ser Asp Thr Asp Ser Asp
                805                 810                 815

Leu Cys Thr Pro Cys Gly Pro Pro Pro Arg Ser Ala Thr Gly Glu Gly
            820                 825                 830

Pro Phe Gly Asp Val Gly Trp Ala Gly Pro Arg Lys
            835                 840

<210> SEQ ID NO 15
<211> LENGTH: 695
<212> TYPE: PRT
<213> ORGANISM: Homo sapiens
<220> FEATURE:
<223> OTHER INFORMATION: human KCNQ4

<400> SEQUENCE: 15

Met Ala Glu Ala Pro Pro Arg Arg Leu Gly Leu Gly Pro Pro Pro Gly
1               5                   10                  15

Asp Ala Pro Arg Ala Glu Leu Val Ala Leu Thr Ala Val Gln Ser Glu
                20                  25                  30

Gln Gly Glu Ala Gly Gly Gly Ser Pro Arg Arg Leu Gly Leu Leu
            35                  40                  45

Gly Ser Pro Leu Pro Pro Gly Ala Pro Leu Pro Gly Pro Gly Ser Gly
    50                  55                  60

Ser Gly Ser Ala Cys Gly Gln Arg Ser Ser Ala Ala His Lys Arg Tyr
65                  70                  75                  80

Arg Arg Leu Gln Asn Trp Val Tyr Asn Val Leu Glu Arg Pro Arg Gly
                85                  90                  95

Trp Ala Phe Val Tyr His Val Phe Ile Phe Leu Leu Val Phe Ser Cys
            100                 105                 110

Leu Val Leu Ser Val Leu Ser Thr Ile Gln Glu His Gln Glu Leu Ala
            115                 120                 125

Asn Glu Cys Leu Leu Ile Leu Glu Phe Val Met Ile Val Val Phe Gly
130                 135                 140

Leu Glu Tyr Ile Val Arg Val Trp Ser Ala Gly Cys Cys Cys Arg Tyr
145                 150                 155                 160

Arg Gly Trp Gln Gly Arg Phe Arg Phe Ala Arg Lys Pro Phe Cys Val
                165                 170                 175
```

```
Ile Asp Phe Ile Val Phe Val Ala Ser Val Ala Val Ile Ala Ala Gly
            180                 185                 190

Thr Gln Gly Asn Ile Phe Ala Thr Ser Ala Leu Arg Ser Met Arg Phe
        195                 200                 205

Leu Gln Ile Leu Arg Met Val Arg Met Asp Arg Arg Gly Gly Thr Trp
    210                 215                 220

Lys Leu Leu Gly Ser Val Val Tyr Ala His Ser Lys Glu Leu Ile Thr
225                 230                 235                 240

Ala Trp Tyr Ile Gly Phe Leu Val Leu Ile Phe Ala Ser Phe Leu Val
                245                 250                 255

Tyr Leu Ala Glu Lys Asp Ala Asn Ser Asp Phe Ser Ser Tyr Ala Asp
            260                 265                 270

Ser Leu Trp Trp Gly Thr Ile Thr Leu Thr Thr Ile Gly Tyr Gly Asp
        275                 280                 285

Lys Thr Pro His Thr Trp Leu Gly Arg Val Leu Ala Ala Gly Phe Ala
    290                 295                 300

Leu Leu Gly Ile Ser Phe Phe Ala Leu Pro Ala Gly Ile Leu Gly Ser
305                 310                 315                 320

Gly Phe Ala Leu Lys Val Gln Glu Gln His Arg Gln Lys His Phe Glu
                325                 330                 335

Lys Arg Arg Met Pro Ala Ala Asn Leu Ile Gln Ala Ala Trp Arg Leu
            340                 345                 350

Tyr Ser Thr Asp Met Ser Arg Ala Tyr Leu Thr Ala Thr Trp Tyr Tyr
        355                 360                 365

Tyr Asp Ser Ile Leu Pro Ser Phe Arg Glu Leu Ala Leu Leu Phe Glu
    370                 375                 380

His Val Gln Arg Ala Arg Asn Gly Gly Leu Arg Pro Leu Glu Val Arg
385                 390                 395                 400

Arg Ala Pro Val Pro Asp Gly Ala Pro Ser Arg Tyr Pro Pro Val Ala
                405                 410                 415

Thr Cys His Arg Pro Gly Ser Thr Ser Phe Cys Pro Gly Glu Ser Ser
            420                 425                 430

Arg Met Gly Ile Lys Asp Arg Ile Arg Met Gly Ser Ser Gln Arg Arg
        435                 440                 445

Thr Gly Pro Ser Lys Gln Gln Leu Ala Pro Pro Thr Met Pro Thr Ser
    450                 455                 460

Pro Ser Ser Glu Gln Val Gly Glu Ala Thr Ser Pro Thr Lys Val Gln
465                 470                 475                 480

Lys Ser Trp Ser Phe Asn Asp Arg Thr Arg Phe Arg Ala Ser Leu Arg
                485                 490                 495

Leu Lys Pro Arg Thr Ser Ala Glu Asp Ala Pro Ser Glu Glu Val Ala
            500                 505                 510

Glu Glu Lys Ser Tyr Gln Cys Glu Leu Thr Val Asp Asp Ile Met Pro
        515                 520                 525

Ala Val Lys Thr Val Ile Arg Ser Ile Arg Ile Leu Lys Phe Leu Val
    530                 535                 540

Ala Lys Arg Lys Phe Lys Glu Thr Leu Arg Pro Tyr Asp Val Lys Asp
545                 550                 555                 560

Val Ile Glu Gln Tyr Ser Ala Gly His Leu Asp Met Leu Gly Arg Ile
                565                 570                 575

Lys Ser Leu Gln Thr Arg Val Asp Gln Ile Val Gly Arg Gly Pro Gly
            580                 585                 590
```

```
Asp Arg Lys Ala Arg Glu Lys Gly Asp Lys Gly Pro Ser Asp Ala Glu
            595                 600                 605

Val Val Asp Glu Ile Ser Met Met Gly Arg Val Val Lys Val Glu Lys
    610                 615                 620

Gln Val Gln Ser Ile Glu His Lys Leu Asp Leu Leu Gly Phe Tyr
625                 630                 635                 640

Ser Arg Cys Leu Arg Ser Gly Thr Ser Ala Ser Leu Gly Ala Val Gln
                645                 650                 655

Val Pro Leu Phe Asp Pro Asp Ile Thr Ser Asp Tyr His Ser Pro Val
                660                 665                 670

Asp His Glu Asp Ile Ser Val Ser Ala Gln Thr Leu Ser Ile Ser Arg
            675                 680                 685

Ser Val Ser Thr Asn Met Asp
    690                 695

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence:sense
      oligonucleotide (7)

<400> SEQUENCE: 16
ctctgaattc caccatgaag gatgtggagt cggg                              34

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence:antisense
      oligonucleotide (8)

<400> SEQUENCE: 17
aatgtctaga atggctaaag aactgctatg cctgg                             35
```

KCNQ5, A NOVEL POTASSIUM CHANNEL

CROSS-REFERENCES TO RELATED APPLICATIONS

The present application claims priority to U.S. Ser. No. 60/190,954, filed Mar. 21, 2000, herein incorporated by reference in its entirety.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Potassium channels are involved in a number of physiological processes, including regulation of heartbeat, dilation of arteries, release of insulin, excitability of nerve cells, and regulation of renal electrolyte transport. Potassium channels are thus found in a wide variety of animal cells such as nervous, muscular, glandular, immune, reproductive, and epithelial tissue. These channels allow the flow of potassium in and/or out of the cell under certain conditions. For example, the outward flow of potassium ions upon opening of these channels makes the interior of the cell more negative, counteracting depolarizing voltages applied to the cell. These channels are regulated, e.g., by calcium sensitivity, voltage-gating, second messengers, extracellular ligands, and ATP-sensitivity.

Potassium channels are made by alpha subunits that fall into 8 families, based on predicted structural and functional similarities (Wei et al., *Neuropharmacology* 35(7):805–829 (1997)). Three of these families (Kv, Eag-related, and KQT, now referred to as KCNQ) share a common motif of six transmembrane domains and are primarily gated by voltage. Two other families, CNG and SK/IK, also contain this motif but are gated by cyclic nucleotides and calcium, respectively. The three other families of potassium channel alpha subunits have distinct patterns of transmembrane domains. Slo family potassium channels (also known as BK channels) have seven transmembrane domains (Meera et al., *Proc. Natl. Acad. Sci. U.S.A.* 94(25):14066–71 (1997)) and are gated by both voltage and calcium or pH (Schreiber et al., *J. Biol. Chem.* 273:3509–16 (1998)). Another family, the inward rectifier potassium channels (Kir), belong to a structural family containing 2 transmembrane domains (see, e.g., Lagrutta et al., *Jpn. Heart. J.* 37:651–660 1996)), and an eighth functionally diverse family (TP, or "two-pore") contains 2 tandem repeats of this inward rectifier motif.

Potassium channels are typically formed by four alpha subunits, and can be homomeric (made of identical alpha subunits) or heteromeric (made of two or more distinct types of alpha subunits). In addition, potassium channels have often been found to contain additional, structurally distinct auxiliary, or beta, subunits (e.g., Kv, Slo, and KCNQ potassium channel families). These beta subunits do not form potassium channels themselves, but instead they act as auxiliary subunits to modify the functional properties of channels formed by alpha subunits. For example, the Kv beta subunits are cytoplasmic and are known to increase the surface expression of Kv channels and/or modify inactivation kinetics of the channel (Heinemann et al., *J. Physiol.* 493:625–633 (1996); Shi et al., *Neuron* 16(4):843–852 (1996)). In another example, the KCNQ family beta subunit, minK, primarily changes activation kinetics (Sanguinetti et al., *Nature* 384:80–83 (1996)).

The KCNQ family of potassium channels was first identified in humans on the basis of inherited mutations that cause the Long QT syndrome (Wang et al., *Nat. Genet.* 12:17–23 (1996)). The mutations were found in a potassium channel, KVLQT1, now known as KCNQ1, that was structurally distinct from previously cloned voltage-gated potassium channels. More recently, it has been discovered that KCNQ1 represents a larger family of structurally similar voltage-gated potassium channels. Three more members of this novel voltage-gated potassium channel family, KCNQ2, KCNQ3, and KCNQ4, have been cloned from humans (Charlier et al., *Nat. Genet.* 18:53–55; Biervert et al., *Science* 279:403–406 (1998); Singh et al., *Nat. Genet.* 18:25–29 (1998); Yang et al., *J. Biol. Chem.* 273:19419–19423 (1998); and Kubisch et al., *Cell* 96:437–446 (1999)). Mutations in each member of the KCNQ gene family have been linked to inherited human disease. For example, KCNQ1 has been linked to the Long QT syndrome, as described above. KCNQ2 and KCNQ3 have been linked to certain forms of epilepsy (Charlier et al., *Nat. Genet.* 18:53–55; Biervert et al., *Science* 279:403–406 (1998); and Singh et al., *Nat. Genet.* 18:25–29 (1998). KCNQ4 has been linked to deafness (Kubisch et al., *Cell* 96:437–446 (1999)).

KCNQ family genes are typically composed of four alpha subunits from a KCNQ family member and can be homomeric or heteromeric (Yang et al., *J. Biol. Chem.* 273:19419–19423 (1998); and Kubisch et al., *Cell* 96:437–446 (1999)). They are found in a variety of tissues and cell types, and contribute to such processes as neuronal excitability and integration, cardiac pacemaking and muscle contraction (Wang et al., *Nat. Genet.* 12:17–23 (1996); Charlier et al., *Nat. Genet.* 18:53–55; Biervert et al., *Science* 279:403–406 (1998); Singh et al., *Nat. Genet.* 18:25–29 (1998); Yang et al., *J. Biol. Chem.* 273:19419–19423 (1998); and Kubisch et al., *Cell* 96:437–446 (1999)). In particular, KCNQ family members contribute to M-currents, which are key to controlling neuronal excitability (Wang et al., *Science* 282:1890–1893 (1998)).

SUMMARY OF THE INVENTION

The present invention thus provides nucleic acids encoding a novel human KCNQ family protein, named KCNQ5. KCNQ5 is a polypeptide that forms outwardly rectifying, voltage-gated potassium channel. KCNQ5 has not been previously cloned or identified.

In one aspect, the present invention provides an isolated nucleic acid encoding a polypeptide comprising an alpha subunit of a KCNQ potassium channel, the polypeptide: (i) forming, with at least one additional KCNQ alpha subunit, a KCNQ potassium channel having the characteristic of voltage-gating; and (ii) comprising a subsequence having at least 65% amino acid sequence identity to amino acids 343 to 640 of SEQ ID NO:4.

In one embodiment, the nucleic acid comprises a nucleotide sequence of SEQ ID NO:1, SEQ ID NO:2, or SEQ ID NO:3. In another embodiment, the nucleic acid selectively hybridizes under moderately stringent hybridization conditions to a nucleotide sequence of SEQ ID NO:1, SEQ ID NO:2, or SEQ ID NO:3. In another embodiment, the nucleic acid is amplified by primers that selectively hybridize under stringent hybridization conditions to the same sequence as the primers selected from the group consisting of:

| | |
|---|---|
| CCACGTCTGCACTCAGGAAGTCTCCG | (SEQ ID NO:6) |
| CCAGCTTGGATTCTATGGACTGTACC | (SEQ ID NO:7) |
| GAAGAGCCGAGAGAAAATAACAGCAG | (SEQ ID NO:8) |
| GCCCTGTGGATAGCAAAGATCTTTCG | (SEQ ID NO:9) |
| GCTGTGAGCATAAACCACTGAACCC | (SEQ ID NO:10) |
| CCATGCGCACCATGCGGAGGATCTG | (SEQ ID NO:11) |
| CATGAAGGATGTGGAGTCGGG | (SEQ ID NO:12) and |
| TGGCTAAAGAACTGCTATGCCTGG | (SEQ ID NO:13). |

In another aspect, the present invention provides an isolated nucleic acid encoding a KCNQ polypeptide, the nucleic acid specifically hybridizing under stringent conditions to a nucleotide sequence of SEQ ID NO:1, SEQ ID NO:2, or SEQ ID NO:3.

In another aspect, the present invention provides an isolated nucleic acid that specifically hybridizes under stringent conditions to a nucleic acid encoding an amino acid sequence of SEQ ID NO:4 or SEQ ID NO:5.

In another aspect, the present invention provides a method of detecting a nucleic acid, the method comprising contacting the nucleic acid with an isolated nucleic acid, as described above.

In another aspect, the present invention provides expression vectors comprising the nucleic acids of the invention, and host cells comprising such expression vectors.

In another aspect, the present invention provides An isolated polypeptide comprising an alpha subunit of a KCNQ potassium channel, the polypeptide: (i) forming, with at least one additional KCNQ alpha subunit, a KCNQ potassium channel having the characteristic of voltage-gating; and (ii) comprising a subsequence having at least 65% amino acid sequence identity to amino acids 343 to 640 of SEQ ID NO:4.

In one embodiment, the polypeptide specifically binds to antibodies generated against SEQ ID NO:4 or SEQ ID NO:5. In another embodiment, the polypeptide has a molecular weight of between about 95 kD to about 104 kD. In another embodiment, the polypeptide has an amino acid sequence of human KCNQ5. In another embodiment, the polypeptide has an amino acid sequence of SEQ ID NO:4 or SEQ ID NO:5.

In one embodiment, the polypeptide comprises an alpha subunit of a homomeric potassium channel. In another embodiment, the polypeptide encoded by the nucleic acid comprises an alpha subunit of a heteromeric potassium channel.

In another aspect, the present invention provides An antibody that specifically binds to the KCNQ polypeptide described herein.

In another aspect, the present invention provides a method for identifying a compound that increases or decreases ion flux through a potassium channel, the method comprising the steps of: (i) contacting the compound with a KCNQ polypeptide, the polypeptide (a) forming, with at least one additional KCNQ alpha subunit, a KCNQ potassium channel having the characteristic of voltage-gating; and (b) comprising a subsequence having at least 65% amino acid sequence identity to amino acids 343 to 640 of SEQ ID NO:4; and (ii) determining the functional effect of the compound upon the potassium channel.

In one embodiment, the functional effect is a physical effect or a chemical effect. In another embodiment, the functional effect is determined by measuring ligand binding to the channel.

In one embodiment, the polypeptide is expressed in a eukaryotic host cell or cell membrane. In another embodiment, the functional effect is determined by measuring ion flux, changes in ion concentrations, changes in current or changes in voltage.

In one embodiment, the polypeptide is recombinant.

In another aspect, the present invention provides a method for identifying a compound that increases or decreases ion flux through a potassium channel comprising a KCNQ5 polypeptide, the method comprising the steps of: (i) entering into a computer system an amino acid sequence of at least 50 amino acids of a KCNQ5 polypeptide or at least 150 nucleotides of a nucleic acid encoding the KCNQ5 polypeptide, the KCNQ5 polypeptide comprising a subsequence having at least 65% amino acid sequence identity to amino acids 343 to 640 of SEQ ID NO:4; (ii) generating a three-dimensional structure of the polypeptide encoded by the amino acid sequence; (iii) generating a three-dimensional structure of the potassium channel comprising the KCNQ5 polypeptide; (iv) generating a three-dimensional structure of the compound; and (v) comparing the three-dimensional structures of the polypeptide and the compound to determine whether or not the compound binds to the polypeptide.

In another aspect, the present invention provides a method of modulating ion flux through a KCNQ potassium channel, the method comprising the step of contacting the KCNQ potassium channel, wherein the channel comprises a KCNQ5 alpha subunit, with an therapeutically effective amount of a compound identified using the methods described herein.

In another aspect, the present invention provides a method of detecting the presence of hKCNQ5 in human tissue, the method comprising the steps of: (i) isolating a biological sample; (ii) contacting the biological sample with an hKCNQ5-specific reagent that selectively associates with hKCNQ5; and, (iii) detecting the level of hKCNQ5-specific reagent that selectively associates with the sample.

In one embodiment, the hKCNQ5-specific reagent is selected from the group consisting of: hKCNQ5-specific antibodies, hKCNQ5-specific oligonucleotide primers, and hKCNQ5-nucleic acid probes.

In another aspect, the present invention provides, in a computer system, a method of screening for mutations of a human KCNQ5 gene, the method comprising the steps of: (i) entering into the computer a first nucleic acid sequence encoding a KCNQ5 polypeptide having a nucleotide sequence of SEQ ID NO:1, SEQ ID NO:2, or SEQ ID NO:3, and conservatively modified versions thereof; (ii) comparing the first nucleic acid sequence with a second nucleic acid sequence having substantial identity to the first nucleic acid sequence; and (iii) identifying nucleotide differences between the first and second nucleic acid sequences.

In one embodiment, the second nucleic acid sequence is associated with a disease state.

In another aspect, the present invention provides, in a computer system, a method for identifying a three-dimensional structure of a KCNQ5 polypeptide, the method comprising the steps of: (i) entering into the computer system an amino acid sequence of at least 50 amino acids of the KCNQ5 polypeptide or at least 150 nucleotides of a nucleic acid encoding the polypeptide, the KCNQ5 polypeptide comprising a subsequence having at least 65% amino acid sequence identity to amino acids 343 to 640 of SEQ ID NO:4; and (ii) generating a three-dimensional structure of the polypeptide encoded by the amino acid sequence.

In one embodiment, the amino acid sequence is a primary structure and wherein said generating step includes the steps of: (i) forming a secondary structure from said primary structure using energy terms determined by the primary structure; and (ii) forming a tertiary structure from said secondary structure using energy terms determined by said secondary structure. In another embodiment, the generating step further includes the step of forming a quaternary structure from said tertiary structure using anisotropic terms encoded by the tertiary structure. In another embodiment, the method further comprises the step of identifying regions of the three-dimensional structure of the polypeptide that bind to ligands and using the regions to identify ligands that bind to a potassium channel comprising a KCNQ5 polypeptide.

BRIEF DESCRIPTION OF THE DRAWINGS

FIG. 1. Amino acid alignment of the deduced amino acid sequence of the KCNQ5 splice variants KCNQ5-1 (SEQ ID NO:4) and KCNQ5-2 (SEQ ID NO:5). Identical residues are shaded and amino acid positions are given at the left margin.

FIG. 2. Amino acid alignment of KCNQ5 (SEQ ID NO:4) with human KCNQ2 (SEQ ID NO:14) (Charlier et al., *Nat. Genet.* 18:53–55 (1988) and KCNQ4 (SEQ ID NO:15) (Kubisch et al., *Cell* 96:437–446 (1999)). Identical residues are shaded and numbers at the left margin indicate amino acid position.

DETAILED DESCRIPTION OF THE INVENTION

Figure 3A:
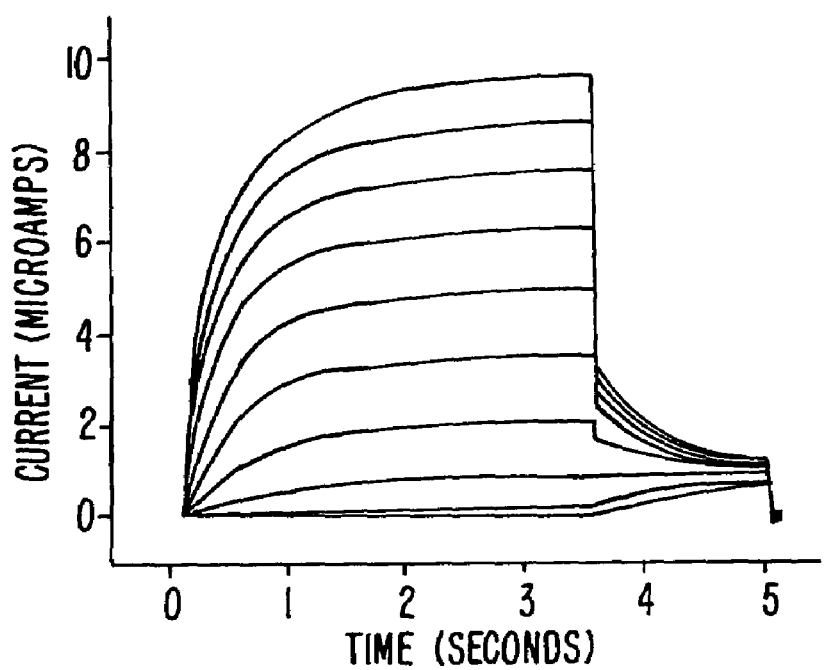
FIG. 3. Expression of KCNQ5 in *Xenopus* oocytes. A). Outward potassium currents recorded from an oocyte expressing the KCNQ5-1 splice variant. The currents were elicited by steps ranging from –90 mV to 10 mV in 10 mV increments from a holding potential of –100 mV. Tail currents were recorded at –60 mV. Similar results were obtained for the KCNQ5-2 splice variant. Note the slow activation and deactivation kinetics, and the presence of current even at hyperpolarized voltages. B) A conductance vs. voltage curve is shown for the traces in (A). The measurements were taken from instantaneous tail currents. The individual data points are fit with a single Boltzmann yielding a half-activation voltage of –50.7 mV.

The present invention provides for the first time nucleic acids encoding human KCNQ5. This polypeptide monomer is a member of the KCNQ family of potassium channels. Members of this family are polypeptide subunits of potassium channels having six transmembrane regions. Expression of the KCNQ5 gene in the *Xenopus* oocyte system produces a slow, outwardly rectifying potassium current. KCNQ5 channels are voltage-gated and are activated by depolarizations above –80 mV (see FIG. 3). These properties suggest a role for the modulation of KCNQ5 in controlling cellular excitability. Increases in the KCNQ5 current will tend to suppress excitatory depolarizations, as potassium efflux through the KCNQ5 channels will lead to hyperpolarization. Conversely, excitability in cells expressing KCNQ5 may be enhanced by blocking or downregulating the KCNQ5 current.

The invention therefore provides methods of screening for activators and inhibitors of potassium channels that contain a KCNQ5 subunit. Such modulators of potassium channel activity are useful for treating disorders, including CNS disorders, such as epilepsy, migraines, hearing and vision problems, psychotic disorders, seizures, learning and memory disorders. Such modulators are also useful as neuroprotective agents (e.g., to prevent stroke) and for treatment of pain.

Furthermore, the invention provides assays for KCNQ5 activity where KCNQ5 acts as a direct or indirect reporter molecule. Such uses of KCNQ5 as a reporter molecule in assay and detection systems have broad applications, e.g., KCNQ5 can be used as a reporter molecule to measure changes in potassium concentration, membrane potential, current flow, ion flux, transcription, signal transduction, receptor-ligand interactions, second messenger concentrations, in vitro, in vivo, and ex vivo. In one embodiment, KCNQ5 can be used as an indicator of current flow in a particular direction (e.g., outward or inward potassium flow), and in another embodiment, KCNQ5 can be used as an indirect reporter via attachment to a second reporter molecule such as green fluorescent protein.

The invention also provides for methods of detecting KCNQ5 nucleic acid and protein expression, allowing investigation of the channel diversity provided by human, as well as diagnosis of disorders, including CNS disorders, such as epilepsy, migraines, hearing and vision problems, psychotic disorders, seizures, learning and memory disorders, stroke, and pain disorders.

Finally, the invention provides for a method of screening for mutations of hKCNQ5 genes or proteins. The invention includes, but is not limited to, methods of screening for mutations in hKCNQ5 with the use of a computer. Similarly, the invention provides for methods of identifying the three-dimensional structure of KCNQ5, as well as the resulting computer readable images or data that comprise the three dimensional structure of KCNQ5. Other methods for screening for mutations of hKCNQ5 genes or proteins include high density oligonucleotide arrays, PCR, immunoassays and the like.

Functionally, KCNQ5 is an alpha subunit of a KCNQ potassium channel. KCNQ5 channels are voltage gated and outwardly rectifying. Typically, such channels are heteromeric or homomeric and contain four alpha subunits or monomers each with six transmembrane domains. Heteromeric KCNQ channels can comprise one or more KCNQ5 alpha subunits along with one or more additional alpha subunits from the KCNQ family. For example, KCNQ5 forms heteromultimeric KCNQ channels with KCNQ3. KCNQ5 channels may also be homomeric. In addition, such channels may comprise one or more auxiliary beta subunits. The presence of KCNQ5 in a potassium channel may also modulate the activity of the heteromeric channel and thus enhance channel diversity. Channel diversity is also enhanced with alternatively spliced forms of KCNQ5 (e.g., KCNQ5-1 and KCNQ5-2). Subsequences of KCNQ5 have been isolated from cDNAs from the human brain, dorsal root ganglion and trigeminal ganglion.

Structurally, the nucleotide sequence of human KCNQ5 (SEQ ID NOS:1–3) encodes a polypeptide monomer with a predicted molecular weight of approximately 99 kD (SEQ ID NOS:4–5, corresponding to polymorphic variants hKCNQ5-1 and hKCNQ5-2) and a predicted molecular weight range of 94–104 kD. In particular, the amino acid sequence of KCNQ5 has a conserved region corresponding to amino acids 343 to 640 of SEQ ID NO:4 (hKCNQ5-1). The alignment of KCNQ5, KCNQ4, and KCNQ2 in FIG. 2 can also be used to selected regions conserved in KCNQ5 but not in other KCNQ polypeptides. Conversely, the alignment can be used to select conserved regions in the KCNQ gene family. Related KCNQ5 genes from other species share at least about 65%, preferably 70%, 75%, 80%, 85%, 90% or 95% amino acid identity in the conserved region.

The present invention also provides polymorphic variants of the hKCNQ5 depicted in SEQ ID NO:4: variant #1, in which an alanine residue is substituted for the glycine residue at amino acid position 36; variant #2, in which a serine residue is substituted for the alanine acid residue at amino acid position 50; variant #3, in which a glycine residue is substituted for the serine residue at amino acid position 446; and variant #4, in which an arginine residue is substituted for the lysine residue at amino acid position 542.

Specific regions of KCNQ5 nucleotide and amino acid sequence may be used to identify polymorphic variants, interspecies homologs, and alleles of hKCNQ5. This identification can be made in vitro, e.g., under stringent hybridization conditions and sequencing, or by using the sequence information in a computer system for comparison with other nucleotide sequences, or using antibodies raised to KCNQ5. Typically, identification of polymorphic variants, orthologs, and alleles of hKCNQ5 is made by comparing the amino acid sequence (or the nucleic acid encoding the amino acid sequence) of a conserved region corresponding to amino acids 343–640 of SEQ ID NO:4. Amino acid identity of approximately at least 65% or above, preferably 70%, 75%, 80%, 85%, most preferably 90–95% or above in the conserved region (amino acids 343–640 of SEQ ID NO:4) typically demonstrates that a protein is a polymorphic variant, interspecies homolog, or allele of hKCNQ5. Sequence comparison is typically performed using the BLAST or BLAST 2.0 algorithm with default parameters, discussed below.

Polymorphic variants, interspecies homologs, and alleles of hKCNQ5 can be confirmed by expressing or co-expressing the putative KCNQ5 polypeptide monomer and examining whether it forms a potassium channel with KCNQ family functional characteristics, and KCNQ5 characteristics such as outward rectification. This assay is used to demonstrate that a protein having about 65% or greater, preferably 70%, 75%, 80%, 85%, 90%, or 95% or greater amino acid identity to the conserved region of KCNQ5 shares the same functional characteristics as KCNQ5 and is therefore a species of KCNQ5. Typically, hKCNQ5 having the amino acid sequence of SEQ ID NO:4 or SEQ ID NO:5 is used as a positive control in comparison to the putative KCNQ5 protein to demonstrate the identification of a polymorphic variant, ortholog, conservatively-modified variant, mutant, or allele of hKCNQ5.

KCNQ5 nucleotide and amino acid sequence information may also be used to construct models of voltage-gated potassium channels in a computer system. These models are subsequently used to identify compounds that can activate or inhibit voltage-gated potassium channels comprising KCNQ5. Such compounds that modulate the activity of channels comprising KCNQ5 can be used to investigate the role of KCNQ5 in modulation of channel activity and in channel diversity.

The isolation of biologically active KCNQ5 for the first time provides a means for assaying for inhibitors and activators of voltage-gated potassium channels that comprise KCNQ5 subunits. Biologically active KCNQ5 is useful for testing inhibitors and activators of voltage-gated potassium channels comprising subunits of KCNQ5 and other Kv members using in vivo and in vitro expression that measure, e.g., changes in voltage or current. Such activators and inhibitors identified using a potassium channel comprising at least one KCNQ5 subunit, optionally four KCNQ5 subunits, can be used to further study voltage gating, channel kinetics and conductance properties of potassium channels. Such activators and inhibitors are useful as pharmaceutical agents for treating diseases involving abnormal ion flux, e.g., disorders, including CNS disorders, such as epilepsy, migraines, hearing and vision problems, psychotic disorders, seizures, learning and memory disorders, stroke, and pain, as described above. Methods of detecting KCNQ5 and expression of channels comprising KCNQ5 are also useful for diagnostic applications for diseases involving abnormal ion flux, e.g., as described above. For example, chromosome localization of the gene encoding human KCNQ5 can be used to identify diseases caused by and associated with KCNQ5. Methods of detecting KCNQ5 are also useful for examining the role of KCNQ5 in channel diversity and modulation of channel activity.

II. Definitions

As used herein, the following terms have the meanings ascribed to them unless specified otherwise.

The phrase "conserved region" refers to the region of KCNQ5 that structurally identifies this particular protein (approximately amino acids 343–640 of SEQ ID NO:4). This region can be used to identify KCNQ5 polymorphic variants, orthologs, conservatively modified variants, mutants, and alleles of KCNQ5, each of will typically comprise at least about 65%, 70%, 75%, 80%, 85%, 90%, 95%, or greater amino acid sequence identity to the conserved region, through amino acid sequence identity comparison using a sequence comparison algorithm such as BLASTP, using the parameters described herein.

"KCNQ5" refers to a polypeptide that is a subunit or monomer of a KCNQ potassium channel, and a member of the KCNQ family. When KCNQ5 is part of a potassium channel, either a homomeric or heteromeric potassium channel, the channel has the characteristic of outward rectification and voltage gating. The term KCNQ5 therefore refers to polymorphic variants, alleles, mutants, and interspecies homologs that: (1) have a subsequence that has greater than about 65% amino acid sequence identity, preferably about 70%, 75%, 80% 85%, 90%, or 95% amino acid sequence identity, to the KCNQ5 conserved region (amino acids 343–640 of SEQ ID NO:4), or, optimally, comprise 65%, 70%, 75%, 80%, 85%, 90%, 95%, or greater identity to an KCNQ5 amino acid sequence of SEQ ID NO:4 or SEQ ID NO:5; (2) bind to antibodies, e.g., polyclonal antibodies, raised against an immunogen comprising an amino acid sequence of SEQ ID NO:4 or SEQ ID NO:5 or amino acids 343–640 of SEQ ID NO:4, and conservatively modified variants thereof; (3) specifically hybridize under stringent hybridization conditions to a sequence of SEQ ID NOS:1–3 or a nucleotide sequence encoding amino acids 343–640 of SEQ ID NO:4, and conservatively modified variants thereof;

or (4) are amplified by primers that specifically hybridize under stringent hybridization conditions to the same sequence as a primer set selected from the group consisting of SEQ ID NOS:6–13.

The phrase "voltage-gated" activity or "voltage-gating" refers to a characteristic of a potassium channel composed of individual polypeptide monomers or subunits. Generally, the probability of a voltage-gated potassium channel opening increases as a cell is depolarized. Voltage-gated potassium channels primarily allow efflux of potassium because they have greater probabilities of being open at membrane potentials more positive than the membrane potential for potassium ($E_K$) in typical cells. $E_K$, or the membrane potential for potassium, depends on the relative concentrations of potassium found inside and outside the cell membrane, and is typically between −60 and −100 mV for mammalian cells. $E_K$ is the membrane potential at which there is no net flow of potassium ion because the electrical potential (i.e., voltage potential) driving potassium influx is balanced by the concentration gradient (the [$K^+$] potential) directing potassium efflux. This value is also known as the "reversal potential" or the "Nernst" potential for potassium. Some voltage-gated potassium channels undergo inactivation, which can reduce potassium efflux at higher membrane potentials. Potassium channels can also allow potassium influx in certain instances when they remain open at membrane potentials negative to $E_K$ (see, e.g., Adams & Nonner, in *Potassium Channels*, pp. 40–60 (Cook, ed., 1990)). The characteristic of voltage gating can be measured by a variety of techniques for measuring changes in current flow and ion flux through a channel, e.g., by changing the [$K^+$] of the external solution and measuring the activation potential of the channel current (see, e.g., U.S. Pat. No. 5,670,335), by measuring current with patch clamp techniques or voltage clamp under different conditions, and by measuring ion flux with radiolabeled tracers or voltage-sensitive dyes under different conditions.

"Homomeric channel" refers to an KCNQ5 channel composed of identical alpha subunits, whereas "heteromeric channel" refers to an KCNQ5 channel composed of at least one KCNQ5 alpha subunit plus at least one other different type of alpha subunit from a related gene family such as the KCNQ family. Both homomeric and heteromeric channels can include auxiliary beta subunits. Typically, the channel is composed of four alpha subunits and the channel can be heteromeric or homomeric.

A "beta subunit" is a polypeptide monomer that is an auxiliary subunit of a potassium channel composed of alpha subunits; however, beta subunits alone cannot form a channel (see, e.g., U.S. Pat. No. 5,776,734). Beta subunits are known, for example, to increase the number of channels by helping the alpha subunits reach the cell surface, change activation kinetics, and change the sensitivity of natural ligands binding to the channels. Beta subunits can be outside of the pore region and associated with alpha subunits comprising the pore region. They can also contribute to the external mouth of the pore region.

The phrase "functional effects" in the context of assays for testing compounds affecting a channel comprising KCNQ5 includes the determination of any parameter that is indirectly or directly under the influence of the channel. It includes physical and chemical effects, e.g., changes in ion flux and membrane potential, changes in ligand binding, and also includes other physiologic effects such as increases or decreases of transcription or hormone release.

"Determining the functional effect" refers to examining the effect of a compound that increases or decreases ion flux on a cell or cell membrane in terms of cell and cell membrane function. The ion flux can be any ion that passes through a channel and analogues thereof, e.g., potassium, rubidium. Preferably, the term refers to the functional effect of the compound on the channels comprising KCNQ5, e.g., changes in ion flux including radioisotopes, current amplitude, membrane potential, current flow, transcription, protein binding, phosphorylation, dephosphorylation, second messenger concentrations (cAMP, cGMP, $Ca^{2+}$, $IP_3$), ligand binding, and other physiological effects such as hormone and neurotransmitter release, as well as changes in voltage and current. Such functional effects can be measured by any means known to those skilled in the art, e.g., patch clamping, voltage-sensitive dyes, whole cell currents, radioisotope efflux, inducible markers, and the like.

"Inhibitors," "activators" or "modulators" of voltage-gated potassium channels comprising KCNQ5 refer to inhibitory or activating molecules identified using in vitro and in vivo assays for KCNQ5 channel function. Inhibitors are compounds that decrease, block, prevent, delay activation, inactivate, desensitize, or down regulate the channel. Activators are compounds that increase, open, activate, facilitate, enhance activation, sensitize or up regulate channel activity. Such assays for inhibitors and activators include e.g., expressing KCNQ5 in cells or cell membranes and then measuring flux of ions through the channel and determining changes in polarization (i.e., electrical potential). Alternatively, cells expressing endogenous KCNQ5 channels can be used in such assays. To examine the extent of inhibition, samples or assays comprising an KCNQ5 channel are treated with a potential activator or inhibitor and are compared to control samples without the inhibitor. Control samples (untreated with inhibitors) are assigned a relative KCNQ5 activity value of 100%. Inhibition of channels comprising KCNQ5 is achieved when the KCNQ5 activity value relative to the control is about 90%, preferably 50%, more preferably 25–0%. Activation of channels comprising KCNQ5 is achieved when the KCNQ5 activity value relative to the control is 110%, more preferably 150%, most preferably at least 200–500% higher or 1000% or higher.

"Biologically active" KCNQ5 refers to KCNQ5 that has the ability to form a potassium channel having the characteristic of voltage-gating tested as described above.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated KCNQ5 nucleic acid is separated from open reading frames that flank the KCNQ5 gene and encode proteins other than KCNQ5. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605–2608 (1985); Rossolini et al., *Mol. Cell. Probes* 8:91–98 (1994)). The term nucleic acid is used interchangeably with gene, cDNA, mRNA, oligonucleotide, and polynucleotide.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. An example of potassium channel splice variants is discussed in Leicher, et al., *J. Biol. Chem.* 273(52): 35095–35101 (1998).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I. The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "label" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins for which antisera or monoclonal antibodies are available (e.g., the polypeptides of SEQ ID NOS:4–5 can be made detectable, e.g., by incorporating a radiolabel into the peptide, and used to detect antibodies specifically reactive with the peptide).

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are preferably directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., 65% identity, preferably 70%, 75%, 80%, 85%, 90%, or 95% identity over a specified region such as the KCNQ5 conserved region (see, e.g., amino acids 343–640 of SEQ ID NO:4), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Preferably, the identity exists over a region that is at least about 25 amino acids or nucleotides in length, or more preferably over a region that is 50–100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins to KCNQ5 nucleic acids and proteins, the BLAST and BLAST 2.0 algorithms and the default parameters discussed below are used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of algorithm that is suitable for determining percent sequence identity and sequence similarity are the BLAST and BLAST 2.0 algorithms, which are described in Altschul et al., *Nuc. Acids Res.* 25:3389–3402 (1977) and Altschul et al., *J. Mol. Biol.* 215:403–410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes,* "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cased, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552–554 (1990))

For preparation of monoclonal or polyclonal antibodies, any technique known in the art can be used (see, e.g., Kohler & Milstein, *Nature* 256:495–497 (1975); Kozbor et al., *Immunology Today* 4: 72 (1983); Cole et al., pp. 77–96 in *Monoclonal Antibodies and Cancer Therapy*, Alan R. Liss, Inc. (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348: 552–554 (1990); Marks et al., *Biotechnology* 10:779–783 (1992)).

An "anti-KCNQ5" antibody is an antibody or antibody fragment that specifically binds a polypeptide encoded by the KCNQ5 gene, cDNA, or a subsequence thereof.

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to KCNQ5, as shown in SEQ ID NOS:4–5, or splice variants, or portions thereof, can be selected to obtain only those polyclonal antibodies that are specifically immunoreactive with KCNQ5 and not with other proteins, except for polymorphic variants, orthologs, and alleles of KCNQ5. This selection may be achieved by subtracting out antibodies that cross-react with molecules such as KCNQ1-4, or other KCNQ orthologs. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo.

"Biological sample" as used herein is a sample of biological tissue or fluid that contains KCNQ5 or nucleic acid encoding KCNQ5 protein. Such samples include, but are not limited to, tissue isolated from humans. Biological samples may also include sections of tissues such as frozen sections taken for histologic purposes. A biological sample is typically obtained from a eukaryotic organism, preferably eukaryotes such as fungi, plants, insects, protozoa, birds, fish, reptiles, and preferably a mammal such as rat, mice, cow, dog, guinea pig, or rabbit, and most preferably a primate such as chimpanzees or humans.

III. Isolating the Gene Encoding KCNQ5

A. General Recombinant DNA Methods

This invention relies on routine techniques in the field of recombinant genetics. Basic texts disclosing the general methods of use in this invention include Sambrook et al., *Molecular Cloning, A Laboratory Manual* (2nd ed, 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kD) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859–1862 (1981), using an automated synthesizer, as described in Van Devanter et. al., *Nucleic Acids Res.* 12:6159–6168 (1984).

Purification of oligonucleotides is by either native acrylamide gel electrophoresis or by anion-exchange HPLC as described in Pearson & Reanier, *J. Chrom.* 255:137–149 (1983).

The sequence of the cloned genes and synthetic oligonucleotides can be verified after cloning using, e.g., the chain termination method for sequencing double-stranded templates of Wallace et al., *Gene* 16:21–26 (1981).

B. Cloning Methods for the Isolation of Nucleotide Sequences Encoding KCNQ5

In general, the nucleic acid sequences encoding KCNQ5 and related nucleic acid sequence homologs are cloned from cDNA and genomic DNA libraries or isolated using amplification techniques with oligonucleotide primers. For example, KCNQ5 sequences are typically isolated from human nucleic acid (genomic or cDNA) libraries by hybridizing with a nucleic acid probe or polynucleotide, the sequence of which can be derived from SEQ ID NOS:1–3, preferably from the region encoding the conserved region (see, e.g., amino acids 343 to 640 of SEQ ID NO:4). A suitable tissue from which KCNQ5 RNA and cDNA can be isolated is nervous system tissue such as whole brain, or skeletal muscle.

Amplification techniques using primers can also be used to amplify and isolate KCNQ5 from DNA or RNA. The following primers can also be used to amplify a sequence of hKCNQ5: CCACGTCTGCACTCAGGAAGTCTCCG (SEQ ID NO:6)

```
CCAGCTTGGATTCTATGGACTGTACC    (SEQ ID NO:7)

GAAGAGCCGAGAGAAAATAACAGCAG    (SEQ ID NO:8)

GCCCTGTGGATAGCAAAGATCTTTCG    (SEQ ID NO:9)

GCTGTGAGCATAAACCACTGAACCC     (SEQ ID NO:10)

CCATGCGCACCATGCGGAGGATCTG     (SEQ ID NO:11)

CATGAAGGATGTGGAGTCGGG         (SEQ ID NO:12) and

TGGCTAAAGAACTGCTATGCCTGG      (SEQ ID NO:13).
```

These primers can be used, e.g., to amplify either the full length sequence or a probe of one to several hundred nucleotides, which is then used to screen a library for full-length KCNQ5.

Nucleic acids encoding KCNQ5 can also be isolated from expression libraries using antibodies as probes. Such polyclonal or monoclonal antibodies can be raised using the sequence of SEQ ID NO:4 or SEQ ID NO:5, or an immunogenic portion thereof, e.g., amino acids 343 to 640 of SEQ ID NO:4.

KCNQ5 polymorphic variants, orthologs, and alleles that are substantially identical to the conserved region of KCNQ5 can be isolated using KCNQ5 nucleic acid probes and oligonucleotides under stringent hybridization conditions, by screening libraries. Alternatively, expression libraries can be used to clone KCNQ5 and KCNQ5 polymorphic variants, orthologs, and alleles by detecting expressed homologs immunologically with antisera or purified antibodies made against hKCNQ5 or portions thereof (e.g., the conserved region of hKCNQ5), which also recognize and selectively bind to the KCNQ5 homolog.

To make a cDNA library, one should choose a source that is rich in hKCNQ5 mRNA, e.g., nervous system tissue such as whole brain, or skeletal muscle. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263–269 (1983); Sambrook et al., supra; Ausubel et al., supra).

For a genomic library, the DNA is extracted from the tissue and either mechanically sheared or enzymatically digested to yield fragments of about 12–20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180–182 (1977). Colony hybridization is carried out as generally described in Grunstein et al., *Proc. Natl. Acad. Sci. USA.*, 72:3961–3965 (1975).

An alternative method of isolating KCNQ5 nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of hKCNQ5 directly from mRNA, from cDNA, from genomic libraries or cDNA libraries. Degenerate oligonucleotides can be designed to amplify KCNQ5 homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of KCNQ5 encoding mRNA in physiological samples, for nucleic acid sequencing, or for other purposes. Genes amplified by the PCR reaction can be purified from agarose gels and cloned into an appropriate vector.

Gene expression of KCNQ5 can also be analyzed by techniques known in the art, e.g., reverse transcription and amplification of mRNA, isolation of total RNA or poly A$^+$ RNA, northern blotting, dot blotting, in situ hybridization, RNase protection, high density polynucleotide array technology and the like.

Synthetic oligonucleotides can be used to construct recombinant KCNQ5 genes for use as probes or for expression of protein. This method is performed using a series of overlapping oligonucleotides usually 40–120 bp in length, representing both the sense and nonsense strands of the gene. These DNA fragments are then annealed, ligated and cloned. Alternatively, amplification techniques can be used with precise primers to amplify a specific subsequence of the KCNQ5 gene. The specific subsequence is then ligated into an expression vector.

The gene for KCNQ5 is typically cloned into intermediate vectors before transformation into prokaryotic or eukaryotic cells for replication and/or expression. These intermediate vectors are typically prokaryote vectors, e.g., plasmids, or shuttle vectors.

C. Expression in Prokaryotes and Eukaryotes

To obtain high level expression of a cloned gene, such as those cDNAs encoding KCNQ5, one typically subclones KCNQ5 into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al., and Ausubel et al, supra. Bacterial expression systems for expressing the KCNQ5 protein are available in, e.g., *E. coli, Bacillus* sp., and *Salmonella* (Palva et al., *Gene* 22:229–235 (1983); Mosbach et al., *Nature* 302:543–545 (1983). Kits for such expression systems are commercially available. Eukaryotic expression systems for mammalian cells, yeast, and insect cells are well known in the art and are also commercially available.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the KCNQ5 encoding nucleic acid in host cells. A typical expression cassette thus contains a promoter operably linked to the nucleic acid sequence encoding KCNQ5 and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A⁺, pMTO10/A⁺, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase and dihydrofolate reductase. Alternatively, high yield expression systems not involving gene amplification are also suitable, such as using a baculovirus vector in insect cells, with a KCNQ5 encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of KCNQ5 protein, which are then purified using standard techniques (see, e.g., Colley et al., *J. Biol. Chem.* 264:17619–17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349–351 (1977); Clark-Curtiss & Curtiss, *Methods in Enzymology* 101:347–362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing KCNQ5.

After the expression vector is introduced into the cells, the transfected cells are cultured under conditions favoring expression of KCNQ5, which is recovered from the culture using standard techniques identified below.

IV. Purification of KCNQ5 Polypeptides

Either naturally occurring or recombinant KCNQ5 can be purified for use in functional assays. Naturally occurring KCNQ5 monomers can be purified, e.g., from human tissue such as whole brain or skeletal muscle and any other source of a KCNQ5 homolog. Recombinant KCNQ5 monomers can be purified from any suitable expression system.

The KCNQ5 monomers may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant KCNQ5 monomers are being purified. For example, proteins having established molecular adhesion properties can be reversible fused to the KCNQ5 monomers. With the appropriate ligand, the KCNQ5 monomers can be selectively adsorbed to a purification column and then freed from the column in a relatively pure form. The fused protein is then removed by enzymatic activity. Finally the KCNQ5 monomers could be purified using immunoaffinity columns.

A. Purification of KCNQ5 Monomers from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of the KCNQ5 monomers inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2–3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human KCNQ monomers are separated from other bacterial proteins by standard separation techniques, e.g., with Ni-NTA agarose resin.

Alternatively, it is possible to purify the KCNQ5 monomers from bacteria periplasm. After lysis of the bacteria, when the KCNQ5 monomers are exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying the KCNQ5 Monomers

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20–30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the KCNQ5 monomers can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The KCNQ5 monomers can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Immunological Detection of KCNQ5

In addition to the detection of KCNQ5 genes and gene expression using nucleic acid hybridization technology, one can also use immunoassays to detect the KCNQ5 monomers. Immunoassays can be used to qualitatively or quantitatively analyze the hKCNQ5 monomers. A general overview of the applicable technology can be found in Harlow & Lane, *Antibodies. A Laboratory Manual* (1988).

A. Antibodies to KCNQ5 Monomers

Methods of producing polyclonal and monoclonal antibodies that react specifically with the KCNQ5 monomers or KCNQ5 monomers from particular species such as hKCNQ5 are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495–497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275–1281 (1989); Ward et al., *Nature* 341:544–546 (1989)).

A number of immunogens comprising portions of KCNQ5 monomers may be used to produce antibodies specifically reactive with KCNQ5 monomers. For example, recombinant KCNQ5 monomers or an antigenic fragment thereof, such as the conserved region (see, e.g., amino acids 343–640 of SEQ ID NO:4), can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511–519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275–1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-KCNQ family proteins and other KCNQ family proteins such as KCNQ1, KCNQ2, KCNQ3, and KCNQ4, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better. Antibodies specific only for a particular KCNQ5 ortholog, such as hKCNQ5, can also be made, by subtracting out other cross-reacting orthologs from a species such as a non-human mammal.

Once the specific antibodies against a KCNQ5 are available, the KCNQ5 can be detected by a variety of immunoassay methods. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

The KCNQ5 can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991). Immunological binding assays (or immunoassays) typically use an antibody that specifically binds to a protein or antigen of choice (in this case the KCNQ5 or an antigenic subsequence thereof). The antibody (e.g., anti-KCNQ5) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled KCNQ5 polypeptide or a labeled anti-KCNQ5 antibody. Alternatively, the labeling agent may be a third moiety, such a secondary antibody, which specifically binds to the antibody/KCNQ5 complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401–1406 (1973); Akerstrom et al., *J. Immunol.* 135:2589–2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting the KCNQ5 in samples may be either competitive or noncompetitive. Noncompetitive immunoassays are assays in which the amount of antigen is directly measured. In one preferred "sandwich" assay, for example, the anti-KCNQ5 subunit antibodies can be bound directly to a solid substrate on which they are immobilized. These immobilized antibodies then capture KCNQ5 present in the test sample. The KCNQ5 monomers are thus immobilized and then bound by a labeling agent, such as a second KCNQ5 antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of the KCNQ5 present in the sample is measured indirectly by measuring the amount of known, added (exogenous) KCNQ5 displaced (competed away) from an anti-KCNQ5 antibody by the unknown KCNQ5 present in a sample. In one competitive assay, a known amount of the KCNQ5 is added to a sample and the sample is then contacted with an antibody that specifically binds to the KCNQ5. The amount of exogenous KCNQ5 bound to the antibody is inversely proportional to the concentration of the KCNQ5 present in the sample. In a particularly preferred embodiment, the antibody is immobilized on a solid substrate. The amount of KCNQ5 bound to the antibody may be determined either by measuring the amount of KCNQ5 present in a KCNQ5/antibody complex, or alternatively by measuring the amount of remaining uncomplexed protein. The amount of KCNQ5 may be detected by providing a labeled KCNQ5 molecule.

A hapten inhibition assay is another preferred competitive assay. In this assay the known KCNQ5 is immobilized on a solid substrate. A known amount of anti-KCNQ5 antibody is added to the sample, and the sample is then contacted with the immobilized KCNQ5. The amount of anti-KCNQ5 antibody bound to the known immobilized KCNQ5 is inversely proportional to the amount of KCNQ5 present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations for KCNQ5. For example, a KCNQ5 protein at least partially corresponding to an amino acid sequence of SEQ ID NO:4 or SEQ ID NO:5 or an immunogenic region thereof, such as the conserved region (e.g., amino acids 343–640 of SEQ ID NO:4), can be immobilized to a solid support. Other proteins such as other KCNQ family members, e.g., KCNQ1, KCNQ2, KCNQ3, and KCNQ4 are added to the assay so as to compete for binding of the antisera to the immobilized antigen. The ability of the added proteins to compete for binding of the antisera to the immobilized protein is compared to the ability of the KCNQ5 or immunogenic portion thereof to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs. Antibodies that specifically bind to particular orthologs of KCNQ5, such as human KCNQ5, can also be made using this methodology.

The immunoabsorbed and pooled antisera are then used in a competitive binding immunoassay as described above to compare a second protein, thought to be perhaps an allele, ortholog, or polymorphic variant of KCNQ5, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by KCNQ5 that is required to inhibit 50% of binding, then the second protein is said to specifically bind to the polyclonal antibodies generated to the respective KCNQ5 immunogen.

Other Assay Formats

Western blot (immunoblot) analysis is used to detect and quantify the presence of the KCNQ5 in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind KCNQ5. The anti-KCNQ5 antibodies specifically bind to KCNQ5 on the solid support. These antibodies may be directly labeled or alternatively may be subsequently detected using labeled antibodies (e.g., labeled sheep anti-mouse antibodies) that specifically bind to the anti-KCNQ5 antibodies.

Other assay formats include liposome immunoassays (LIA), which use liposomes designed to bind specific molecules (e.g., antibodies) and release encapsulated reagents or markers. The released chemicals are then detected according to standard techniques (see, Monroe et al., *Amer. Clin. Prod. Rev.* 5:34–41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), which is either inherently detectable or covalently bound to a signal system, such as a detectable enzyme, a fluorescent compound, or a chemiluminescent compound. The ligands and their targets can be used in any suitable combination with antibodies that recognize hKCNQ5, or secondary antibodies that recognize anti-hKCNQ5 antibodies.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally, simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Assays for Modulators of KCNQ5

A. Assays

Human KCNQ5 monomers and KCNQ5 alleles, orthologs, and polymorphic variants are subunits of potassium channels. The activity of a potassium channel comprising KCNQ5 can be assessed using a variety of in vitro and in vivo assays, e.g., measuring current, measuring membrane potential, measuring ion flux, e.g., potassium, or rubidium, measuring ion concentration, measuring second messengers and transcription levels, using potassium-dependent yeast growth assays, measuring ligand binding, and using, e.g., voltage-sensitive dyes, ion sensitive dyes such as potassium sensitive dyes, radioactive tracers, and patch-clamp electrophysiology.

Furthermore, such assays can be used to test for inhibitors and activators of channels comprising KCNQ5. Such modulators of a potassium channel are useful for treating various disorders involving potassium channels. Treatment of dysfunctions include, e.g., CNS disorders, such as epilepsy, migraines, hearing and vision problems, psychotic disorders, seizures, learning and memory disorders. Such modulators are also useful as neuroprotective agents (e.g., to prevent stroke) and for treatment of pain. Such modulators are also useful for investigation of the channel diversity provided by hKCNQ5 and the regulation/modulation of potassium channel activity provided by hKCNQ5.

Modulators of the KCNQ potassium channels are tested using biologically active KCNQ5, either recombinant or naturally occurring, preferably hKCNQ5. KCNQ5 can be isolated, co-expressed or expressed in a cell, or expressed in a membrane derived from a cell. In such assays, KCNQ5 is expressed alone to form a homomeric potassium channel or is co-expressed with a second alpha subunit (e.g., another KCNQ family member) so as to form a heteromeric potassium channel. KCNQ5 can also be expressed with additional beta subunits. Modulation is tested using one of the in vitro or in vivo assays described above. Samples or assays that are treated with a potential potassium channel inhibitor or activator are compared to control samples without the test compound, to examine the extent of modulation. Control samples (untreated with activators or inhibitors) are assigned a relative potassium channel activity value of 100. Inhibition of channels comprising KCNQ5 is achieved when the potassium channel activity value relative to the control is about 90%, preferably 50%, more preferably 25%. Activation of channels comprising KCNQ5 is achieved when the potassium channel activity value relative to the control is 110%, more preferably 150%, more preferable 200% higher. Compounds that increase the flux of ions will cause a detectable increase in the ion current density by increasing the probability of a channel comprising KCNQ5 being open, by decreasing the probability of it being closed, by increasing conductance through the channel, and/or by allowing the passage of ions.

Changes in ion flux may be assessed by determining changes in polarization (i.e., electrical potential) of the cell or membrane expressing the potassium channel comprising KCNQ5. A preferred means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include: radio-labeled rubidium flux assays and fluorescence assays using voltage-sensitive dyes (see, e.g., Vestergarrd-Bogind et al, *J. Membrane Biol.* 88:67–75 (1988); Daniel et al., *J. Pharmacol. Meth.* 25:185–193 (1991); Holevinsky et al., *J. Membrane Biology* 137:59–70 (1994)). Assays for compounds capable of inhibiting or increasing potassium flux through the channel proteins comprising KCNQ5 can be performed by application of the compounds to a bath solution in contact with and comprising cells having a channel of the present invention (see, e.g., Blatz et al., *Nature* 323:718–720 (1986); Park, *J. Physiol.* 481:555–570 (1994)). Generally, the compounds to be tested are present in the range from 1 pM to 100 mM.

The effects of the test compounds upon the function of the channels can be measured by changes in the electrical currents or ionic flux or by the consequences of changes in currents and flux. Changes in electrical current or ionic flux are measured by either increases or decreases in flux of ions such as potassium or rubidium ions. The ions can be measured in a variety of standard ways. They can be measured directly by concentration changes of the ions, e.g., changes in intracellular concentrations, or indirectly by membrane potential or by radio-labeling of the ions. Consequences of the test compound on ion flux can be quite varied. Accordingly, any suitable physiological change can be used to assess the influence of a test compound on the channels of this invention. The effects of a test compound can be measured by a toxin binding assay. When the functional consequences are determined using intact cells or animals, one can also measure a variety of effects such as transmitter release (e.g., dopamine), intracellular calcium changes, hormone release (e.g., insulin), transcriptional changes to both known and uncharacterized genetic markers (e.g., northern blots), cell volume changes (e.g., in red blood cells), immunoresponses (e.g., T cell activation), changes in cell metabolism such as cell growth or pH changes, and changes in intracellular second messengers such as cyclic nucleotides.

Preferably, the KCNQ5 polypeptide that is a part of the potassium channel used in the assay will have the sequence displayed in SEQ ID NO:4 or SEQ ID NO:5 or a conservatively modified variant thereof. Alternatively, the KCNQ5 of the assay will be derived from a eukaryote and include an amino acid subsequence having substantial amino acid sequence identity to the conserved region (see, e.g., amino acids 343 to 640 of SEQ ID NO:4) of hKCNQ5. Generally, the amino acid sequence identity will be at least 65%, preferably at least 70%, 75%, 80%, 85%, or 90%, most preferably at least 95%.

KCNQ5 orthologs, alleles, polymorphic variants, and conservatively modified variants will generally confer substantially similar properties on a channel comprising KCNQ5, as described above. In a preferred embodiment, the cell placed in contact with a compound that is suspected to be a KCNQ5 homolog is assayed for increasing or decreasing ion flux in a eukaryotic cell, e.g., an oocyte of Xenopus (e.g., Xenopus laevis) or a mammalian cell such as a CHO or HeLa cell. Channels that are affected by compounds in ways similar to KCNQ5 are considered homologs or orthologs of KCNQ5.

B. Modulators

The compounds tested as modulators of KCNQ channels comprising a KCNQ5 subunit can be any small chemical compound, or a biological entity, such as a protein, sugar, nucleic acid or lipid. Alternatively, modulators can be genetically altered versions of a KCNQ5 subunit. Typically, test compounds will be small chemical molecules and peptides. Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al, *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274: 1520–1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the cell or tissue expressing a KCNQ channel comprising a human KCNQ5 subunit is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds are possible using the integrated systems of the invention.

C. Solid State and Soluble High throughput Assays

In one embodiment the invention provide soluble assays using potassium channels comprising KCNQ5; a membrane comprising a KCNQ5 potassium channel, or a cell or tissue expressing potassium channels comprising KCNQ5, either naturally occurring or recombinant. In another embodiment, the invention provides solid phase based in vitro assays in a high throughput format, where KCNQ5 potassium channel attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100- about 1500 different compounds. It is possible to assay many plates per day; assay screens for up to about 6,000, 20,000, 50,000, or more than 100,000 different compounds is possible using the integrated systems of the invention.

The channel of interest, or a cell or membrane comprising the channel of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the taste transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

VII. Computer Assisted Drug Design Using hKCNQ5

Yet another assay for compounds that modulate the activities of KCNQ5 involves computer assisted drug design, in which a computer system is used to generate a three-dimensional structure of KCNQ5 based on the structural information encoded by the amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind, e.g., ligands or other potassium channel subunits. These regions are then used to identify ligands that bind to the protein or region where KCNQ5 interacts with other potassium channel subunits.

The three-dimensional structural model of the protein is generated by entering channel protein amino acid sequences of at least 25, 50, 75 or 100 amino acid residues or corresponding nucleic acid sequences encoding an KCNQ5 monomer into the computer system. The amino acid sequence of each of the monomers is selected from the group consisting of SEQ ID NO:4 or SEQ ID NO:5 and a conservatively modified versions thereof, or an immunogenic portion thereof comprising amino acids 343–640 of SEQ ID NO:4. The amino acid sequence represents the primary sequence or subsequence of each of the proteins, which encodes the structural information of the protein. At least 25, 50, 75, or 100 residues of the amino acid sequence (or a nucleotide sequence encoding at least about 25, 50, 75 or 100 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the channel protein is then generated by the interaction of the amino acid sequence and the computer system, using software known to those of skill in the art. The resulting three-dimensional computer model can then be saved on a computer readable substrate.

The amino acid sequence represents a primary structure that encodes the information necessary to form the secondary, tertiary and quaternary structure of the monomer and the heteromeric potassium channel protein comprising four monomers. The software looks at certain parameters encoded by the primary sequence to generate the structural model. These parameters are referred to as "energy terms," or anisotropic terms and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of KCNQ5 protein to identify ligands that bind to KCNQ5. Binding affinity between the protein and ligands is determined using energy terms to determine which ligands have an enhanced probability of binding to the protein.

Computer systems are also used to screen for mutations, polymorphic variants, alleles and interspecies homologs of KCNQ5 genes. Such mutations can be associated with disease states. Once the variants are identified, diagnostic assays can be used to identify patients having such mutated genes associated with disease states. Identification of the mutated KCNQ5 genes involves receiving input of a first nucleic acid, e.g., SEQ ID NOS:1–3, or an amino acid sequence encoding KCNQ5, selected from the group consisting of SEQ ID NOS:4–5, and conservatively modified versions thereof, or an amino acid sequence comprising amino acids 343–640 of SEQ ID NO:4. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in KCNQ5 genes, preferably hKCNQ5 genes, and mutations associated with disease states. The first and second sequences described above can be saved on a computer readable substrate.

Nucleic acids encoding KCNQ5 monomers can be used with high density oligonucleotide array technology (e.g., GeneChip™) to identify homologs and polymorphic variants of KCNQ5 in this invention. In the case where the homologs being identified are linked to a known disease, they can be used with GeneChip™ as a diagnostic tool in detecting the disease in a biological sample, see, e.g., Gunthand et al., *AIDS Res. Hum. Retroviruses* 14: 869–876 (1998); Kozal et al., *Nat. Med.* 2:753–759 (1996); Matson et al., *Anal. Biochem.* 224:110–106 (1995); Lockhart et al., *Nat. Biotechnol.* 14:1675–1680 (1996); Gingeras et al., *Genome Res.* 8:435–448 (1998); Hacia et al., *Nucleic Acids Res.* 26:3865–3866 (1998).

VIII. Cellular Transfection and Gene Therapy

The present invention provides the nucleic acids of KCNQ5 for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid for KCNQ5, under the control of a promoter, then expresses a KCNQ5 monomer of the present invention, thereby mitigating the effects of absent, partial inactivation, or abnormal expression of the KCNQ5 gene.

Such gene therapy procedures have been used to correct acquired and inherited genetic defects, cancer, and viral infection in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808–813 (1992); Nabel & Felgner, TIBTECH 11:211–217 (1993); Mitani & Caskey, TIBTECH 11:162–166 (1993); Mulligan, *Science* 926–932 (1993); Dillon, TIBTECH 11:167–175 (1993); Miller, *Nature* 357: 455–460 (1992); Van Brunt, *Biotechnology* 6(10):1149–1154 (1998); Vigne, *Restorative Neurology and Neuroscience* 8:35–36 (1995); Kremer & Perricaudet, *British Medical Bulletin* 51(1):31–44 (1995); Haddada et al., in *Current Topics in Microbiology and Immunology* (Doerfler & Böhm eds., 1995); and Yu et al., *Gene Therapy* 1 :13–26 (1994)).

Delivery of the gene or genetic material into the cell is the first step in gene therapy treatment of disease. A large number of delivery methods are well known to those of skill in the art. Preferably, the nucleic acids are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell.

Methods of non-viral delivery of nucleic acids include lipofection, microinjection, biolistics, virosomes, liposomes, immunoliposomes, polycation or lipid:nucleic acid conjugates, naked DNA, artificial virions, and agent-enhanced uptake of DNA. Lipofection is described in, e.g., U.S. Pat. No. 5,049,386, U.S. Pat. No. 4,946,787; and U.S. Pat. No. 4,897,355 and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404–410 (1995); Blaese et al., *Cancer Gene Ther.* 2:291–297 (1995); Behr et al., *Bioconjugate Chem.* 5:382–389 (1994); Remy et al., *Bioconjugate Chem.*

5:647–654 (1994); Gao et al., *Gene Therapy* 2:710–722 (1995); Ahmad et al., *Cancer Res.* 52:4817–4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vector that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6–10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), simian immunodeficiency virus (SIV), human immunodeficiency virus (HIV), and combinations thereof (see, e.g., Buchscher et al., *J. Virol.* 66:2731–2739 (1992); Johann et al., *J. Virol.* 66:1635–1640 (1992); Sommerfelt et al., *Virol.* 176:58–59 (1990); Wilson et al., *J. Virol.* 63:2374–2378 (1989); Miller et al., *J. Virol.* 65:2220–2224 (1991); PCT/US94/05700).

In applications where transient expression of the nucleic acid is preferred, adenoviral based systems are typically used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38–47 (1987); U.S. Pat. No. 4,797,368; WO 93/24641; Kotin, *Human Gene Therapy* 5:793–801 (1994); Muzyczka, *J. Clin. Invest.* 94:1351 (1994)). Construction of recombinant AAV vectors are described in a number of publications, including U.S. Pat. No. 5,173,414; Tratschin et al., *Mol. Cell. Biol.* 5:3251–3260 (1985); Tratschin et al., *Mol. Cell. Biol.* 4:2072–2081 (1984); Hermonat & Muzyczka, *Proc. Natl. Acad. Sci. U.S.A.* 81:6466–6470 (1984); and Samulski et al., *J. Virol.* 63:03822–3828 (1989).

In particular, at least six viral vector approaches are currently available for gene transfer in clinical trials, with retroviral vectors by far the most frequently used system. All of these viral vectors utilize approaches that involve complementation of defective vectors by genes inserted into helper cell lines to generate the transducing agent.

pLASN and MFG-S are examples are retroviral vectors that have been used in clinical trials (Dunbar et al., *Blood* 85:3048–305 (1995); Kohn et al., *Nat. Med.* 1:1017–102 (1995); Malech et al., *Proc. Natl. Acad. Sci. U.S.A.* 94:22 12133–12138 (1997)). PA317/pLASN was the first therapeutic vector used in a gene therapy trial. (Blaese et al., *Science* 270:475–480 (1995)). Transduction efficiencies of 50% or greater have been observed for MFG-S packaged vectors (Ellem et al., *Immunol Immunother.* 44(l):10–20 (1997); Dranoff et al., *Hum. Gene Ther.* 1:111–2 (1997)).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system (Wagner et al., *Lancet* 351:9117 1702–3 (1998), Kearns et al., *Gene Ther.* 9:748–55 (1996)).

Replication-deficient recombinant adenoviral vectors (Ad) are predominantly used transient expression gene therapy, because they can be produced at high titer and they readily infect a number of different cell types. Most adenovirus vectors are engineered such that a transgene replaces the Ad E1a, E1b, and E3 genes; subsequently the replication defector vector is propagated in human 293 cells that supply deleted gene function in trans. Ad vectors can transduce multiple types of tissues in vivo, including nondividing, differentiated cells such as those found in the liver, kidney and muscle system tissues. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083–9 (1998)). Additional examples of the use of adenovirus vectors for gene transfer in clinical trials include Rosenecker et al., *Infection* 241: 5–10 (1996); Sterman et al., *Hum. Gene Ther.* 9:7 1083–1089 (1998); Welsh et al., *Hum. Gene Ther.* 2:205–18 (1995); Alvarez et al., *Hum. Gene Ther.* 5:597–613 (1997); Topfet al., *Gene Ther.* 5:507–513 (1998); Sterman et al., *Hum. Gene Ther.* 7:1083–1089 (1998).

In many gene therapy applications, it is desirable that the gene therapy vector be delivered with a high degree of specificity to a particular tissue type. A viral vector is typically modified to have specificity for a given cell type by expressing a ligand as a fusion protein with a viral coat protein on the viruses outer surface. The ligand is chosen to have affinity for a receptor known to be present on the cell type of interest. For example, Han et al., *Proc. Natl. Acad. Sci. U.S.A.* 92:9747–9751 (1995), reported that Moloney murine leukemia virus can be modified to express human heregulin fused to gp70, and the recombinant virus infects certain human breast cancer cells expressing human epidermal growth factor receptor. This principle can be extended to other pairs of virus expressing a ligand fusion protein and target cell expressing a receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences thought to favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

Vectors (e.g., retroviruses, adenoviruses, liposomes, etc.) containing therapeutic nucleic acids can be also administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

Administration is by any of the routes normally used for introducing a molecule into ultimate contact with blood or tissue cells. The nucleic acids are administered in any suitable manner, preferably with pharmaceutically acceptable carriers. Suitable methods of administering such nucleic acids are available and well known to those of skill in the art, and, although more than one route can be used to administer a particular composition, a particular route can often provide a more immediate and more effective reaction than another route.

IX. Pharmaceutical Compositions and Administration

Pharmaceutically acceptable carriers are determined in part by the particular composition being administered (e.g., nucleic acid, protein, modulatory compounds or transduced cell), as well as by the particular method used to administer the composition. Accordingly, there are a wide variety of suitable formulations of pharmaceutical compositions of the present invention (see, e.g., *Remington's Pharmaceutical Sciences*, 17$^{th}$ ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of the KCNQ channels comprising a KCNQ5 subunit, the physician evaluates circulating plasma levels of the vector, vector toxicities, progression of the disease, and the production of anti-vector antibodies. In general, the dose equivalent of a naked nucleic acid from a vector is from about 1 μg to 100 μg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

X. Kits

Human KCNQ5 and its homologs are useful tools for examining expression and regulation of potassium channels. Human KCNQ5-specific reagents that specifically hybridize to hKCNQ5 nucleic acid, such as hKCNQ5 probes and primers, and hKCNQ5-specific reagents that specifically bind to the hKCNQ5 protein, e.g., hKCNQ5 antibodies are used to examine expression and regulation.

Nucleic acid assays for the presence of hKCNQ5 DNA and RNA in a sample include numerous techniques are known to those skilled in the art, such as Southern analysis, northern analysis, dot blots, RNase protection, S1 analysis, amplification techniques such as PCR and LCR, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology,* vol. VII, pp. 189–226 (1984); and *Nucleic Acid Hybridization: A Practical Approach* (Hames et al., eds. 1987). In addition, hKCNQ5 protein can be detected with the various immunoassay techniques described above. The test sample is typically compared to both a positive control (e.g., a sample expressing recombinant KCNQ5 monomers) and a negative control.

The present invention also provides for kits for screening modulators of the potassium channels of the invention. Such kits can be prepared from readily available materials and reagents. For example, such kits can comprise any one or more of the following materials: KCNQ5 monomers, reaction tubes, and instructions for testing the activities of potassium channels containing KCNQ5. A wide variety of kits and components can be prepared according to the present invention, depending upon the intended user of the kit and the particular needs of the user. For example, the kit can be tailored for in vitro or in vivo assays for measuring the activity of a potassium channel comprising a KCNQ5 monomer.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following example is provided by way of illustration only and not by way of limitation. Those of skill in the art will readily recognize a variety of noncritical parameters that could be changed or modified to yield essentially similar results.

Example 1

Cloning of KCNQ5

A 1.15 kb clone from the middle of KCNQ5 was amplified from human brain cDNA. The sense primer was (1) 5'-CCACGTCTGCACTCAGGAAGTCTCCG (SEQ ID NO:6) and the antisense primer was (2) 5'-CCAGCTTG-GATTCTATGGACTGTACC (SEQ ID NO:7). The complete 3' end of KCNQ5 was amplified by standard 3' RACE PCR techniques from human brain cDNA in two successive rounds. In the first round the gene specific primer used was (3) 5'-GAAGAGCCGAGAGAAAATAACAGCAG (SEQ ID NO:8). This reaction was reamplified with the gene-specific oligo (4) 5'-GCCCTGTGGATAGCAAA-GATCTTTCG (SEQ ID NO:9) to obtain a 1.2 kb fragment that contained the entire 3' region of the KCNQ5 mRNA.

The 5' end of KCNQ5 was amplified from human brain cDNA using 2 nested rounds of a standard 5' RACE PCR. The gene specific oligos used in the first and second amplifications were (5) 5'-GCTGTGAGCATAAACCACT-GAACCC (SEQ ID NO:10) and (6) 5'-CCATGCGCAC-CATGCGGAGGATCTG (SEQ ID NO:11), respectively. A 650 bp fragment containing the missing 5' end of the KCNQ5 coding region was isolated from the second reaction.

The entire coding region of KCNQ5 was then isolated in a single fragment using oligonucleotides overlapping the KCNQ5 coding sequence ends as determined from sequence analysis of the above fragments. The oligonucleotides were (7) 5'-CTCTGAATTCCACCATGAAGGATGTG-GAGTCGGG (SEQ ID NO:16) (sense) and (8) 5'-AAT-GTCTAGAATGGCTAAAGAACTGCTATGCCTGG (SEQ ID NO:17) (antisense). The first oligonucleotide includes the initiator methionine and first 20 coding nucleotides of the KCNQ5 gene. Upstream are an EcoRI restriction enzyme site for subcloning into plasmid vectors and a Kozak consensus sequence to boost translation. All nucleotides corresponding to KCNQ5 are in bold type. The second oligonucleotide is from the 3' untranslated sequence of KCNQ5 and includes an Xba1 restriction site for subcloning. Non-KCNQ5 sequences at the 5' end of each primer were included for expression vector construction, but these sequences are not necessary for the amplification of the KCNQ5 gene. Only those sequences shown in bold type, which are from KCNQ5 itself, are needed to amplify KCNQ5 when using these particular primers. The preferred template for the amplification is first strand cDNA made from some part of the human brain, or whole brain. Whole human brain cDNA was used for this reaction.

The amplification conditions used were as follows: 24 cycles of 96° C. for 20 seconds, 70–58° C. for 15 seconds (temperature was dropped 0.5° C. each successive cycle), 72° C. for 3 minutes, followed by 20 cycles of 96° C. for 20 seconds, 58° C. for 15 seconds and 72° C. for 3 minutes. An approximately 3 kb band corresponding to the entire coding region of KCNQ5 was obtained and confirmed by sequencing. Two distinct KCNQ5 variants were sequenced, KCNQ5-1 and KCNQ5-2. The difference between the clones is that a 27 nucleotide segment of present in KCNQ5-1 and the originally determined KCNQ5 sequence is absent in KCNQ5-2. An alignment of the deduced amino acid sequences of each clone is shown in FIG. 1.

All of the numbered oligonucleotides listed above can be used in combination to amplify various sections of the KCNQ5 gene's coding region using the conditions described above. 1 can be used with 2 to produce the 1.15 kb band described above, or 1 can be used with 8 to amplify an approximately 2.2 kb fragment extending from the KCNQ5 S4 through the KCNQ5 stop codon. 2 can also be used with 7 to produce an approximately 1.8 kb fragment that includes the 5' end of KCNQ5. 3 or 4 can be used with 8 to produce an approximately 700 bp fragment that includes the 3' end of KCNQ5. 5 or 6 can be used with 7 to produce an approximately 640 bp product from the 5' end of KCNQ5. It should be noted that 7 and 8 need only include the sequences given above in bold type. Note that all fragment sizes are approximate.

Figure 4:
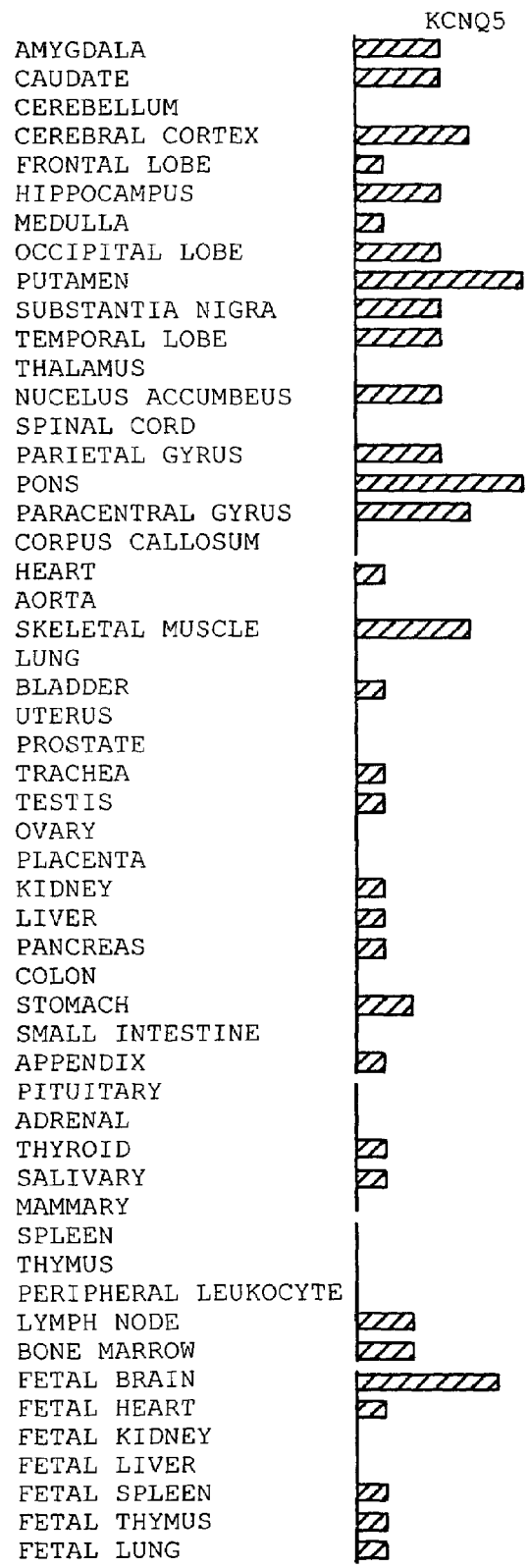
FIG. 4. mRNA distribution for KCNQ5. Data was generated by hybridizing a $^{32}$P-labeled KCNQ5 probe against human mRNA samples from the indicated tissues fixed to a nylon filter. Bars show relative expression level in the tissues indicated. Highest expression was seen in the pons and putamen. High level expression of KCNQ5 is limited to the nervous system with the exception of skeletal muscle. KCNQ5 expression is high in both fetal and adult brain. KCNQ5 expression was also detected by RT-PCR in dorsal root ganglion and trigeminal ganglion, two tissues not represented on the mRNA used to generate this data.

An alignment of the deduced amino acid sequence of KCNQ5 to previously cloned human KCNQ family genes (KCNQ2, KCNQ3, KCNQ4) is shown in FIG. 2. The predicted molecular weight of the KCNQ5 protein is about 99 kD. mRNA expression of KCNQ5 is shown in FIG. 4.

Example 2

Expression of KCNQ5 in *Xenopus* Oocytes

Figure 3B:
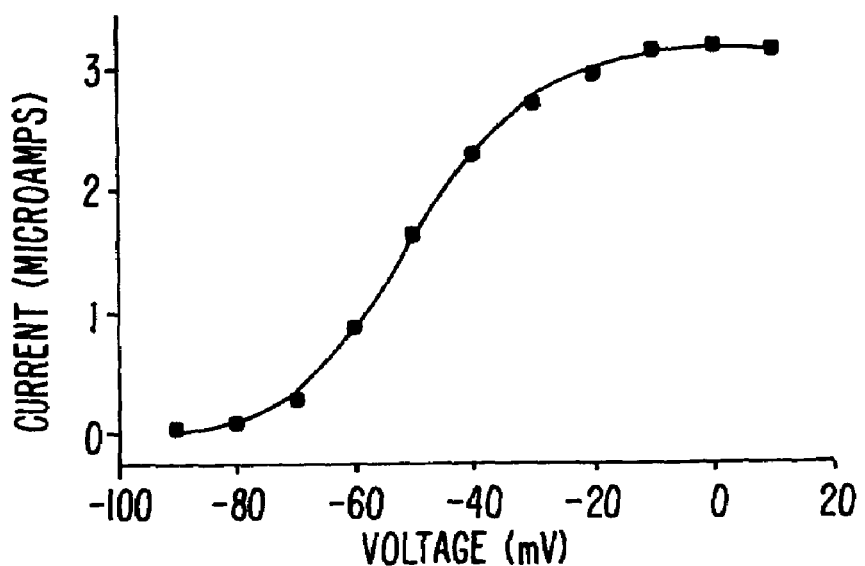

Expression of the KCNQ5 gene in the *Xenopus* oocyte system produces a slow outwardly-rectifying potassium current that is activated by voltages as low as −80 mV (FIG. 3). These properties suggest a role for the modulation of KCNQ5 in controlling cellular excitability. Increases in the KCNQ5 current will tend to suppress excitatory depolarizations because potassium efflux through the KCNQ5 channels will lead to hyperpolarization. Conversely, excitability in cells expressing KCNQ5 may be enhanced by blocking or downregulating the KCNQ5 current.

What is claimed is:

1. An isolated nucleic acid having a nucleotide sequence selected from the group consisting of SEQ ID NO: 1, SEQ ID NO: 2, and SEQ ID NO: 3, wherein said nucleic acid encodes a polypeptide comprising an alpha subunit of a KCNQ potassium channel, wherein said polypeptide forms, with at least one additional KCNQ alpha subunit, a KCNQ potassium channel having the characteristic of voltage-gating.

2. The nucleic acid of claim 1, wherein the polypeptide encoded by the nucleic acid comprises an alpha subunit of a homomeric potassium channel.

3. The nucleic acid of claim 1, wherein the polypeptide encoded by the nucleic acid comprises an alpha subunit of a heteromeric potassium channel.

4. An expression vector comprising a nucleic acid of claim 1.

5. An isolated host cell transfected with the vector of claim 4.

* * * * *